US008652459B2

(12) United States Patent
Fleury et al.

(10) Patent No.: US 8,652,459 B2
(45) Date of Patent: Feb. 18, 2014

(54) SPLITTING GP41

(75) Inventors: Sylvain Fleury, Ch Bottens (FR); Morgane Bomsel, Paris (FR)

(73) Assignees: Mymetics Corporation, New York, NY (US); Inserm, Paris (FR)

( * ) Notice: Subject to any disclaimer, the term of this patent is extended or adjusted under 35 U.S.C. 154(b) by 52 days.

(21) Appl. No.: 13/143,873

(22) PCT Filed: Feb. 8, 2010

(86) PCT No.: PCT/EP2010/051524
§ 371 (c)(1), (2), (4) Date: Aug. 17, 2011

(87) PCT Pub. No.: WO2010/089402
PCT Pub. Date: Aug. 12, 2010

(65) Prior Publication Data

US 2011/0311614 A1 Dec. 22, 2011

Related U.S. Application Data

(60) Provisional application No. 61/202,219, filed on Feb. 6, 2009, provisional application No. 61/272,661, filed on Oct. 16, 2009.

(51) Int. Cl.
*A61K 39/21* (2006.01)
*A61K 48/00* (2006.01)

(52) U.S. Cl.
USPC ........................ 424/93.1; 424/188.1; 530/350

(58) Field of Classification Search
None
See application file for complete search history.

(56) References Cited

FOREIGN PATENT DOCUMENTS

| | | | |
|---|---|---|---|
| WO | WO 03/075849 | A2 | 9/2003 |
| WO | WO 2005/010033 | A1 | 2/2005 |
| WO | WO 2006/117586 | A1 | 11/2006 |
| WO | WO 2007/099387 | A1 | 9/2007 |
| WO | WO 2007/099446 | A2 | 9/2007 |

OTHER PUBLICATIONS

Montero et al. Macrobiol. and Molecular Biology Reviews, Mar. 2008, vol. 72, No. 1, pp. 54-84.*
Ho. et al. Vaccine, 2005, vol. 23, No. 13, pp. 1559-1573.*
Matoba et al., "Humoral immune responses by prime-boost heterologous route immunizations with CTB-MPR $_{649-684}$, a Mucosal subunit HIV/AIDS vaccine candidate", *Vaccine*, vol. 24, 2006, pp. 5047-5055.
Matoba et al., "Transcytosis-Blocking Abs Elicited by an Oligomeric Immunogen Based on the Membrane Proximal Region of HIV-1 gp41 Target Non-Neutralizing Epitopes", *Current HIV Research*, vol. 6, 2008, pp. 218-229.
Bomsel et al., "P19-02. High protection of female macaques from repeated intravaginal challenges with SHIV-162p3 upon Mucosal vaccination with Gp41 subunits-verisomes", *AIDS Vaccine*, 2009, pp. 1.
International Preliminary Report on Patentability issued in Application No. PCT/EP2010/051524 dated Aug. 9, 2011.

* cited by examiner

*Primary Examiner* — Bao Li
(74) *Attorney, Agent, or Firm* — Oliff PLC

(57) ABSTRACT

The present invention deals with a method for therapeutic or prophylactic treatment of HIV, in particular a prophylactic vaccinal method, comprising at least: administering to a patient a first antigen comprising the broadly neutralizing epitopes of the Membrane Proximal Ectodomain Region (MPER) of gp41, and administering to the same patient a second antigen comprising a modified polypeptide comprising three contiguous segments N, L and C represented by the formula N-L-C and comprising: a N-helix region of gp41(N), a C-helix region of gp41(C), and a connecting loop comprising a synthetic linker (L) between the N and C-helices, the linker replacing amino acids 593-617 of gp41, the numbering scheme being based upon the prototypic isolate HIV-1 HxB2 Clade B strain, said polypeptide comprising the calveolin-1 neutralizing and 98.6 D epitopes, but not 2F5 and 4E10 epitopes, not the fusion peptide, the polypeptide having a minimal immunogenic cross-reactivity with human interleukin 2.

12 Claims, 8 Drawing Sheets

A

B

SEQUENCE LISTING

```
<160> NUMBER OF SEQ ID NOS: 40

<210> SEQ ID NO 1
<211> LENGTH: 142
<212> TYPE: PRT
<213> ORGANISM: Homo sapiens

<400> SEQUENCE: 1

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Lys Leu Ile
    50                  55                  60

Cys Thr Thr Ala Val Pro Trp Asn Ala Ser Trp Ser Asn Lys Ser Leu
65                  70                  75                  80

Glu Gln Ile Trp Asn His Thr Thr Trp Met Glu Trp Asp Arg Glu Ile
                85                  90                  95

Asn Asn Tyr Thr Ser Leu Ile His Ser Leu Ile Glu Glu Ser Gln Asn
            100                 105                 110

Gln Gln Glu Lys Asn Glu Gln Glu Leu Leu Glu Leu Asp Lys Trp Ala
        115                 120                 125

Ser Leu Trp Asn Trp Phe Asn Ile Thr Asn Trp Leu Trp Tyr
    130                 135                 140


<210> SEQ ID NO 2
<211> LENGTH: 35
<212> TYPE: PRT
<213> ORGANISM: Artificial Sequence
<220> FEATURE:
<223> OTHER INFORMATION: Synthetic Construct: P1 clade B without S

<400> SEQUENCE: 2

Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys
        35
```

-continued

<210> SEQ ID NO 3
<211> LENGTH: 35
<212> TYPE: PRT
<213> ORGANISM: Artificial Sequence
<220> FEATURE:
<223> OTHER INFORMATION: Synthetic Construct: P1 clade C type without spacer

<400> SEQUENCE: 3

```
Ser Gln Thr Gln Gln Glu Lys Asn Glu Gln Glu Leu Leu Ala Leu Asp
1               5                   10                  15

Ser Trp Lys Asn Leu Trp Asn Trp Phe Ser Ile Thr Asn Trp Leu Trp
            20                  25                  30

Tyr Ile Lys
        35
```

<210> SEQ ID NO 4
<211> LENGTH: 38
<212> TYPE: PRT
<213> ORGANISM: Artificial Sequence
<220> FEATURE:
<223> OTHER INFORMATION: Synthetic Construct: P1 clade B with S LGC

<400> SEQUENCE: 4

```
Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys Leu Gly Cys
        35
```

<210> SEQ ID NO 5
<211> LENGTH: 38
<212> TYPE: PRT
<213> ORGANISM: Artificial Sequence
<220> FEATURE:
<223> OTHER INFORMATION: Synthetic Construct: P1 clade B with S LSC

<400> SEQUENCE: 5

```
Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys Leu Ser Cys
        35
```

<210> SEQ ID NO 6
<211> LENGTH: 37
<212> TYPE: PRT
<213> ORGANISM: Artificial Sequence
<220> FEATURE:
<223> OTHER INFORMATION: Synthetic Construct: P1 clade C type with S

<400> SEQUENCE: 6

```
Ser Gln Thr Gln Gln Glu Lys Asn Glu Gln Leu Leu Ala Leu Asp Ser
1               5                   10                  15

Trp Lys Asn Leu Trp Asn Trp Phe Ser Ile Thr Asn Trp Leu Trp Tyr
            20                  25                  30

Ile Lys Leu Gly Cys
        35
```

<210> SEQ ID NO 7
<211> LENGTH: 16

-continued

<212> TYPE: PRT
<213> ORGANISM: Artificial Sequence
<220> FEATURE:
<223> OTHER INFORMATION: Synthetic Construct: 2F5 epitope

<400> SEQUENCE: 7

Asn Glu Gln Glu Leu Leu Glu Leu Asp Lys Trp Ala Ser Leu Trp Asn
1 5 10 15

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct: Calveolin binding domain

<400> SEQUENCE: 8

Ser Leu Glu Gln Ile Trp Asn Asn Met Thr Trp Met Gln Trp Asp Lys
1 5 10 15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct: Spacer

<400> SEQUENCE: 9

Leu Glu His Ser His His His
1 5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct: Spacer with cysteine

<400> SEQUENCE: 10

Leu Glu His Ser His His His Cys
1 5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct: Spacer

<400> SEQUENCE: 11

Leu Glu His His His His
1 5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct: Spacer with cysteine

<400> SEQUENCE: 12

Leu Glu His His His His Cys
1 5

<210> SEQ ID NO 13
<211> LENGTH: 54
<212> TYPE: PRT
<213> ORGANISM: Homo sapiens

<400> SEQUENCE: 13

Met Gln Ala Arg Gln Leu Leu Ser Gly Ile Val Gln Gln Gln Asn Asn
1 5 10 15

Leu Leu Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr
35 40 45

Leu Lys Asp Gln Gln Leu
50

<210> SEQ ID NO 14
<211> LENGTH: 54
<212> TYPE: PRT
<213> ORGANISM: Homo sapiens

<400> SEQUENCE: 14

Met Gln Ala Arg Gln Leu Leu Ser Gly Ile Val Gln Gln Gln Asn Asn
1 5 10 15

Leu Asp Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr
35 40 45

Leu Lys Asp Gln Gln Leu
50

<210> SEQ ID NO 15
<211> LENGTH: 47
<212> TYPE: PRT
<213> ORGANISM: Homo sapiens

<400> SEQUENCE: 15

Ser Leu Glu Gln Ile Trp Asn His Thr Thr Trp Met Glu Trp Asp Arg
1 5 10 15

Glu Ile Asn Asn Tyr Thr Ser Leu Ile His Ser Leu Ile Glu Glu Ser
20 25 30

Gln Asn Gln Gln Glu Lys Asn Glu Gln Glu Leu Leu Glu Leu Asp
35 40 45

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct: Linker

<400> SEQUENCE: 16

Ser Gly Gly Arg Gly Gly Ser
1 5

<210> SEQ ID NO 17
<211> LENGTH: 108
<212> TYPE: PRT
<213> ORGANISM: Homo sapiens

<400> SEQUENCE: 17

Met Gln Ala Arg Gln Leu Leu Ser Gly Ile Val Gln Gln Gln Asn Asn
1 5 10 15

Leu Leu Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr

```
        35                  40                  45

Leu Lys Asp Gln Gln Leu Ser Gly Gly Arg Gly Gly Ser Ser Leu Glu
    50                  55                  60

Gln Ile Trp Asn His Thr Thr Trp Met Glu Trp Asp Arg Glu Ile Asn
65                  70                  75                  80

Asn Tyr Thr Ser Leu Ile His Ser Leu Ile Glu Glu Ser Gln Asn Gln
                85                  90                  95

Gln Glu Lys Asn Glu Gln Glu Leu Leu Glu Leu Asp
            100                 105


<210> SEQ ID NO 18
<211> LENGTH: 108
<212> TYPE: PRT
<213> ORGANISM: Homo sapiens

<400> SEQUENCE: 18

Met Gln Ala Arg Gln Leu Leu Ser Gly Ile Val Gln Gln Gln Asn Asn
1               5                   10                  15

Leu Asp Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Ser Gly Gly Arg Gly Gly Ser Ser Leu Glu
    50                  55                  60

Gln Ile Trp Asn His Thr Thr Trp Met Glu Trp Asp Arg Glu Ile Asn
65                  70                  75                  80

Asn Tyr Thr Ser Leu Ile His Ser Leu Ile Glu Glu Ser Gln Asn Gln
                85                  90                  95

Gln Glu Lys Asn Glu Gln Glu Leu Leu Glu Leu Asp
            100                 105


<210> SEQ ID NO 19
<211> LENGTH: 115
<212> TYPE: PRT
<213> ORGANISM: Homo sapiens

<400> SEQUENCE: 19

Met Gln Ala Arg Gln Leu Leu Ser Gly Ile Val Gln Gln Gln Asn Asn
1               5                   10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln Gln Leu Ser Gly Gly Arg Gly Gly Ser Ser Leu Glu
    50                  55                  60

Gln Ile Trp Asn His Thr Thr Trp Met Glu Trp Asp Arg Glu Ile Asn
65                  70                  75                  80

Asn Tyr Thr Ser Leu Ile His Ser Leu Ile Glu Glu Ser Gln Asn Gln
                85                  90                  95

Gln Glu Lys Asn Glu Gln Glu Leu Leu Glu Leu Asp Leu Glu His His
            100                 105                 110

His His Cys
        115


<210> SEQ ID NO 20
<211> LENGTH: 116
<212> TYPE: PRT
<213> ORGANISM: Homo sapiens
```

<400> SEQUENCE: 20

Met Gln Ala Arg Gln Leu Leu Ser Gly Ile Val Gln Gln Gln Asn Asn
1 5 10 15

Leu Leu Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr
35 40 45

Leu Lys Asp Gln Gln Leu Ser Gly Gly Arg Gly Gly Ser Ser Leu Glu
50 55 60

Gln Ile Trp Asn His Thr Thr Trp Met Glu Trp Asp Arg Glu Ile Asn
65 70 75 80

Asn Tyr Thr Ser Leu Ile His Ser Leu Ile Glu Glu Ser Gln Asn Gln
85 90 95

Gln Glu Lys Asn Glu Gln Glu Leu Leu Glu Leu Asp Leu Glu His Ser
100 105 110

His His His Cys
115

<210> SEQ ID NO 21
<211> LENGTH: 348
<212> TYPE: DNA
<213> ORGANISM: Homo sapiens

<400> SEQUENCE: 21
atgcaggcca gacaattatt gtctggtata gtgcagcagc agaacaattt gctgagggct 60
attgaggcgc aacagcatct gttgcaactc acagtctggg gcatcaagca gctccaggca 120
agaatcctgg ctgtggaaag atacctaaag gatcaacagc tcagtggagg tagaggtgga 180
tcctctctgg aacagatttg gaatcacacg acctggatgg agtgggacag agaaattaac 240
aattacacaa gcttaataca ctccttaatt gaagaatcgc aaaaccagca agaaaagaat 300
gaacaagaat tattggaatt agatctggaa cattctcatc accactgc 348

<210> SEQ ID NO 22
<211> LENGTH: 32
<212> TYPE: DNA
<213> ORGANISM: Artificial Sequence
<220> FEATURE:
<223> OTHER INFORMATION: Synthetic Construct: Primer gp41 Nde1

<400> SEQUENCE: 22
ggaatccaca tatgcaggcc agacaattat tg 32

<210> SEQ ID NO 23
<211> LENGTH: 50
<212> TYPE: DNA
<213> ORGANISM: Artificial Sequence
<220> FEATURE:
<223> OTHER INFORMATION: Synthetic Construct: Primer gp41-Bam1

<400> SEQUENCE: 23
accgttggat ccacctctac ctccactgag ctgttgatcc tttaggtatc 50

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct: Primer gp41-Bam2

<400> SEQUENCE: 24

-continued

```
ggaatccagg atcctctctg gaacagattt ggaatcac                          38


<210> SEQ ID NO 25
<211> LENGTH: 45
<212> TYPE: DNA
<213> ORGANISM: Artificial Sequence
<220> FEATURE:
<223> OTHER INFORMATION: Synthetic Construct: Primer gp41-Xho1

<400> SEQUENCE: 25

gcccggctcg agatctaatt ccaataattc ttgttcattc ttttc                  45


<210> SEQ ID NO 26
<211> LENGTH: 411
<212> TYPE: DNA
<213> ORGANISM: Homo sapiens

<400> SEQUENCE: 26

atgcaggcca gacaattatt gtctggtata gtgcagcagc agaacaattt gctgagggct     60

attgaggcgc aacagcatct gttgcaactc acagtctggg gcatcaagca gctccaggca    120

agaatcctgg ctgtggaaag atacctaaag gatcaacagc tcctggggat ttggggtagc    180

tctggaaaac tcattagcac cactgctgtg ccttggaatg ctagttggag taataaatct    240

ctggaacaga tttggaatca cacgacctgg atggagtggg acagagaaat taacaattac    300

acaagcttaa tacactcctt aattgaagaa tcgcaaaacc agcaagaaaa gaatgaacaa    360

gaattattgg aattagataa atgggcaagt ttgtggaatt ggtttaacat a             411


<210> SEQ ID NO 27
<211> LENGTH: 330
<212> TYPE: DNA
<213> ORGANISM: Homo sapiens

<400> SEQUENCE: 27

atgcaggcca gacaattatt gtctggtata gtgcagcagc agaacaattt gctgagggct     60

attgaggcgc aacagcatct gttgcaactc acagtctggg gcatcaagca gctccaggca    120

agaatcctgg ctgtggaaag atacctaaag gatcaacagc tcagtggagg tagaggtgga    180

tcctctctgg aacagatttg gaatcacacg acctggatgg agtgggacag agaaattaac    240

aattacacaa gcttaataca ctccttaatt gaagaatcgc aaaaccagca agaaaagaat    300

gaacaagaat tattggaatt agatctcgag                                     330


<210> SEQ ID NO 28
<211> LENGTH: 345
<212> TYPE: DNA
<213> ORGANISM: Homo sapiens

<400> SEQUENCE: 28

atgcaggcca gacaattatt gtctggtata gtgcagcagc agaacaattt gctgagggct     60

attgaggcgc aacagcatct gttgcaactc acagtctggg gcatcaagca gctccaggca    120

agaatcctgg ctgtggaaag atacctaaag gatcaacagc tcagtggagg tagaggtgga    180

tcctctctgg aacagatttg gaatcacacg acctggatgg agtgggacag agaaattaac    240

aattacacaa gcttaataca ctccttaatt gaagaatcgc aaaaccagca agaaaagaat    300

gaacaagaat tattggaatt agatctggaa catcatcacc actgc                    345


<210> SEQ ID NO 29
<211> LENGTH: 34
```

<212> TYPE: DNA
<213> ORGANISM: Artificial Sequence
<220> FEATURE:
<223> OTHER INFORMATION: Synthetic Construct: Prime gp41B-C-D1

<400> SEQUENCE: 29
taattccata tgcaggccag acaattattg tctg 34

<210> SEQ ID NO 30
<211> LENGTH: 42
<212> TYPE: DNA
<213> ORGANISM: Artificial Sequence
<220> FEATURE:
<223> OTHER INFORMATION: Synthetic Construct: Primer gp41B-C-R2

<400> SEQUENCE: 30
attccgctcg agttattagc agtggtgatg agaatgttcc ag 42

<210> SEQ ID NO 31
<211> LENGTH: 45
<212> TYPE: DNA
<213> ORGANISM: Artificial Sequence
<220> FEATURE:
<223> OTHER INFORMATION: Synthetic Construct: Primer gp41B-C-R1

<400> SEQUENCE: 31
gtgatgagaa tgttccagat ctaattccaa taattcttgt tcatt 45

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct: Primer T7 prom

<400> SEQUENCE: 32
taatacgact cactataggg 20

<210> SEQ ID NO 33
<211> LENGTH: 19
<212> TYPE: DNA
<213> ORGANISM: Artificial Sequence
<220> FEATURE:
<223> OTHER INFORMATION: Synthetic Construct: Primer T7 term

<400> SEQUENCE: 33
gctagttatt gctcagcgg 19

<210> SEQ ID NO 34
<211> LENGTH: 45
<212> TYPE: DNA
<213> ORGANISM: Artificial Sequence
<220> FEATURE:
<223> OTHER INFORMATION: Synthetic Construct: Primer gp41B-C3-R1

<400> SEQUENCE: 34
gtgatgagaa tgttccagat ctaattccaa taattcttgt tcatt 45

<210> SEQ ID NO 35
<211> LENGTH: 42
<212> TYPE: DNA
<213> ORGANISM: Artificial Sequence
<220> FEATURE:
<223> OTHER INFORMATION: Synthetic Construct: Primer gp41B-C3-R2

<400> SEQUENCE: 35
attccgctcg agttattagc agtggtgatg agaatgttcc ag 42

-continued

<210> SEQ ID NO 36
<211> LENGTH: 390
<212> TYPE: DNA
<213> ORGANISM: Homo sapiens

<400> SEQUENCE: 36
atgcaggcca gacaattatt gtctggtata gtgcagcagc agaacaattt gctgagggct 60
attgaggcgc aacagcatct gttgcaactc acagtctggg gcatcaagca gctccaggca 120
agaatcctgg ctgtggaaag atacctaaag gatcaacagc tcctggggat tgacggtagc 180
agtggaggta gaggtggatc caatgctagt tggagtaata aatctctgga acagatttgg 240
aatcacacga cctggatgga gtgggacaga gaaattaaca attacacaag cttaatacac 300
tccttaattg aagaatcgca aaaccagcaa gaaaagaatg aacaagaatt attggaatta 360
gatctcgagc accaccacca ccaccactga 390

<210> SEQ ID NO 37
<211> LENGTH: 129
<212> TYPE: PRT
<213> ORGANISM: Homo sapiens

<400> SEQUENCE: 37

Met Gln Ala Arg Gln Leu Leu Ser Gly Ile Val Gln Gln Gln Asn Asn
1 5 10 15

Leu Leu Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr
35 40 45

Leu Lys Asp Gln Gln Leu Leu Gly Ile Asp Gly Ser Ser Gly Gly Arg
50 55 60

Gly Gly Ser Asn Ala Ser Trp Ser Asn Lys Ser Leu Glu Gln Ile Trp
65 70 75 80

Asn His Thr Thr Trp Met Glu Trp Asp Arg Glu Ile Asn Asn Tyr Thr
85 90 95

Ser Leu Ile His Ser Leu Ile Glu Glu Ser Gln Asn Gln Gln Glu Lys
100 105 110

Asn Glu Gln Glu Leu Leu Glu Leu Asp Leu Glu His His His His His
115 120 125

His

<210> SEQ ID NO 38
<211> LENGTH: 110
<212> TYPE: PRT
<213> ORGANISM: Homo sapiens

<400> SEQUENCE: 38

Met Gln Ala Arg Gln Leu Leu Ser Gly Ile Val Gln Gln Gln Asn Asn
1 5 10 15

Leu Leu Arg Ala Ile Glu Ala Gln Gln His Leu Leu Gln Leu Thr Val
20 25 30

Trp Gly Ile Lys Gln Leu Gln Ala Arg Ile Leu Ala Val Glu Arg Tyr
35 40 45

Leu Lys Asp Gln Gln Leu Ser Gly Gly Arg Gly Gly Ser Ser Leu Glu
50 55 60

Gln Ile Trp Asn His Thr Thr Trp Met Glu Trp Asp Arg Glu Ile Asn
65 70 75 80

-continued

```
Asn Tyr Thr Ser Leu Ile His Ser Leu Ile Glu Glu Ser Gln Asn Gln
                85                  90                  95

Gln Glu Lys Asn Glu Gln Glu Leu Leu Glu Leu Asp Leu Glu
            100                 105                 110


<210> SEQ ID NO 39
<211> LENGTH: 166
<212> TYPE: PRT
<213> ORGANISM: Artificial Sequence
<220> FEATURE:
<223> OTHER INFORMATION: Synthetic Construct

<400> SEQUENCE: 39

Gly Ala Leu Phe Leu Gly Phe Leu Gly Ala Ala Gly Ser Thr Met Gly
1               5                   10                  15

Ala Ala Ser Met Thr Leu Thr Val Gln Ala Arg Gln Leu Leu Ser Gly
            20                  25                  30

Ile Val Gln Gln Gln Asn Asn Leu Leu Arg Ala Ile Glu Ala Gln Gln
        35                  40                  45

His Leu Leu Gln Leu Thr Val Trp Gly Ile Lys Gln Leu Gln Ala Arg
    50                  55                  60

Ile Leu Ala Val Glu Arg Tyr Leu Lys Asp Gln Gln Leu Leu Gly Ile
65                  70                  75                  80

Trp Gly Cys Ser Gly Lys Leu Ile Cys Thr Thr Ala Val Pro Trp Asn
                85                  90                  95

Ala Ser Trp Ser Asn Lys Ser Leu Glu Gln Ile Trp Asn His Thr Thr
            100                 105                 110

Trp Met Glu Trp Asp Arg Glu Ile Asn Asn Tyr Thr Ser Leu Ile His
        115                 120                 125

Ser Leu Ile Glu Glu Ser Gln Asn Gln Gln Glu Lys Asn Glu Gln Glu
    130                 135                 140

Leu Leu Glu Leu Asp Lys Trp Ala Ser Leu Trp Asn Trp Phe Asn Ile
145                 150                 155                 160

Thr Asn Trp Leu Trp Tyr
                165


<210> SEQ ID NO 40
<211> LENGTH: 37
<212> TYPE: PRT
<213> ORGANISM: Artificial Sequence
<220> FEATURE:
<223> OTHER INFORMATION: Synthetic Construct

<400> SEQUENCE: 40

Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys Leu Ser
        35
```

SPLITTING GP41

Virosome-like vesicles comprising gp41-derived antigens The present invention relates to a novel virosome-like vesicle suitable for inducing an immune response against a human immunodeficiency virus (HIV), pharmaceutical compositions comprising said virosome-like vesicles, methods of treatment and kits for inducing an immune response against a human immunodeficiency virus.

BACKGROUND OF THE INVENTION

The HIV-1 is a retrovirus that gradually destroys the immune system and ultimately leads to the Acquired Immunodeficiency Syndrome (AIDS). A hallmark of the virus is its extremely rapid mutation within a single patient. Genomic mapping of current HIV-1 strains has resulted in a family tree, at the root of which there are three groups called M, N and O, group M being responsible for the current AIDS pandemic.

Group M is split into nine genetic subtypes, also called nine clades (designated A through K, with no E or I). The original definition of clades was based on short genomic sequences, mostly within the HIV envelope protein (Env: gpI60). These nine clades have uneven geographic distribution patterns. Clade C circulates in South Africa, India and parts of China. Clade A and D are common in East Africa and clade B is common in North & South America and Western Europe. The four clades A, B, C and D account for over 90% of all infections worldwide, and clade C represents the world's most dominant HIV (about >60%). Until recently, vaccine development focused on clade B strains, which dominate the epidemic in industrialized countries but cause only about 12% of infections globally.

Most of the vaccine approaches against HIV-1 have targeted the viral envelope (Env) glycoproteins because they are the major surface antigens expressed on virions and by HIV-1 infected cells. The native HIV-1 envelope glycoprotein is an heterotrimer containing three gpI20 proteins non-covalently associated with three gp41 glycoproteins.

Because of the rapid mutation within a single patient, virus-neutralizing antibodies to one variant do not usually protect the patient against HIV, as non-recognized mutants quickly emerge. However, a number of broadly neutralizing antibodies have been discovered, capable of neutralizing a variety of strains from Clade B. The four most potent HIV-1 neutralizing antibodies yet identified: bI2 and 2G12 against the gp120 and 2F5 and 4E10 against the a region of gp41 called the membrane-proximal external region (MPER). These antibodies have a high affinity for the native trimer. However, antibodies capable of cross-clade neutralization are extremely rare. 2F5 reacts well with clade B strains but poorly with clade C strains, 2G12 does not neutralize viruses from clade C of E, and b12 neutralizes 50% of viruses. 4E10 is capable of neutralizing an extremely broad range of HIV-1 primary isolates, from virtually all subtypes, although it appears to have modest potency.

There is an increasing effort to develop recombinant proteins as candidate vaccines that are better antigenic mimics than the native envelope glycoprotein complex gpI20/gp41. However, due to numerous (at least fifteen) molecular homologies between the gpI20/gp41 and molecules of the immune system, many potential cross-reactivities events may occur leading to possible harmful autoimmune phenomena.

Various strategies have been described in order to dampen those cross-reactivities for obtaining anti-HIV vaccines with fewer or no cross reactivities with human proteins, such as the introduction of mutations and/or deletions in various part of the gp41 proteins as described in U.S. Pat. No. 6,455,265.

HIV infections occur mostly at mucosal sites of entry, such as the vagina and anorectal mucosa. Most of the neutralizing antibodies that have been described or induced by the above vaccine strategies are systemic IgG antibodies. However, in women frequently exposed to multiple HIV-1 strains, mucosal IgA antibodies have been found in vaginal secretions and they appear to broadly protect against HIV infection (Broliden, K., et al. 2009, Immunol. Lett. 79, 29-36). Therefore, there is a need for a vaccine capable of inducing such mucosal antibodies.

There is also a need for the development of non-clade B vaccines, such as, for example, clade C strains.

There is also a need for the development of a vaccine with broad inhibitory spectrum allowing for cross-clade inhibition.

There is a need for a vaccine inducing a humoral and/or cellular immune response against HIV infection.

There is a need for a vaccine inducing an immune response against HIV-1 infection both at the mucosal surface level and at the blood level.

There is a need for a vaccine suitable for inducing mucosal IgG and secretory IgA (sIgA) antibodies and systemic IgG antibodies capable of interfering with HIV-1 entry across the mucosa and early cell infection under the mucosa.

There is a need for a vaccine suitable for inhibiting or reducing HIV entry across mucosal tissues through various mechanisms such as transcytosis.

1

It is an object of the invention to satisfy to all those above-mentioned needs.

Therefore, according to one of its first aspect, the present invention is related to a method for therapeutic or prophylactic treatment of HIV, in particular a prophylactic vaccinal method, comprising at least: administering to a patient a first antigen comprising the broadly neutralizing epitopes of the Membrane Proximal External Region (MPER) of gp41, and administering to the same patient a second antigen comprising a modified polypeptide comprising three contiguous segments N, L and C represented by the formula N-L-C and comprising : a N-helix region of gp41(N), a C-helix region of gp41(C), and a connecting loop comprising a synthetic linker (L) between the N and C-helices, the linker replacing amino acids 593-617 of gp41, the numbering scheme being based upon the prototypic isolate HIV-1 HxB2 Clade B strain, said polypeptide comprising the calveolin-1 neutralizing and 98.6 D epitopes, but not 2F5 and 4E10 epitopes, not the fusion peptide, the polypeptide having a minimal immunogenic cross-reactivity with human interleukin 2.

Thus an HIV vaccine according to the invention exhibits, as a property, an ability of eliciting immune responses (CTL and/or antibodies) in the blood as well as at the primary entry sites, which are the reproductive-genital tracts and intestinal/rectal mucosal tissues. This property is particularly advantageous, because HIV infection may comprise a viral transcytosis step on mucosal surface that facilitates virus translocation and spreading into the body.

Semen and cervico-vaginal secretions may potentially transmit HIV-1 to the gastrointestinal, anorectal and genitourinary tracts because they contain cell-free HIV-1 particles and numerous HIV-infected mononuclear cells.

It is also believed that the major site of early viral replication in HIV-infected subjects is the intestine and other mucosal sites. This is mainly because the vast majority of susceptible cells (intestinal CD4+ T cells) reside in mucosal tissues and within the first few weeks post-HIV exposure, these cells are destroyed. Within the meaning of the invention, the expression "virosome-like vesicle" is intended to mean a vesicle comprising at least in part virosomal lipids and fusion proteins or fragments thereof, said fragments having the fusion activity and characteristics of the complete fusion protein, at least in an extent serving for the fusion with a biological membrane of the target cell.

GP41-Derived Antigen

A gp41-derived antigen suitable for the instant invention may be any part of the gp41 protein, as well as the gp41 protein in its whole, and analogues thereof.

Within the meaning of the invention, the expression "analogue thereof with respect to a gp41-derived antigen intends to refer to a peptide having substantial (at least) 85%, in particular at least 90% and more particularly at least 95% amino acid sequence identity or homology (i.e. amino acid residue replaced with an amino acid residue of the same family, of similar polarity or charge, for example) with the amino-acid sequence of said gp41-derived antigen, and which has similar or conserved biological properties, in particular with respect to binding antigen portion of immunoglobulin directed to the gp41 protein.

According to an embodiment, a gp41-derived antigen suitable for the invention may be devoid of fusogenic property with respect to cell membrane.

Within one aspect of the invention there is provided a first antigen comprising the neutralizing epitopes of the Membrane Proximal Ectodomain Region (MPER) of gp41.

According to the present invention, said first antigen comprises the 2F5 and 4E10 epitopes.

In the meaning of the present invention, the 2F5 epitope corresponds to a specific region of gp41 recognized by the human 2F5 antibody which has a broad neutralizing activity for diverse primary HIV-1 isolates (Trkola A. et al., 1995, J. Virol., 69, pp 6609-6617, see FIG. 1). This monoclonal antibody recognizes a core epitope of six amino acids within a relatively conserved 16-amino-acid linear sequence (NEQELLELDKWASLWN, SEQ ID No.7) in the ectodomain of gp41 near the transmembrane region of the molecule (Parker et al., 2001, J. Virol., 75, pp 10906-10911).

The 4E10 human monoclonal antibody is specific for the transmembrane proximal region of gp41 in a location immediately nearby carboxy terminal to the 2F5 epitope and also has a broad neutralizing activity (Zwick et al., 2001, J. Virol., 75, pp 10892-10905, see FIG. 1).

According to an aspect of the invention, the first antigen corresponds to to amino-acids 649-683 of gp41.

In a further embodiment said first antigen comprises a neutralizing IgA epitope.

In a more preferred embodiment of the invention, said first antigen comprises an amino acid sequence described by SEQ ID No 2, SEQ ID No 3, SEQ ID No 4, SEQ ID No 5, or SEQ ID No.6.

In a further preferred aspect, first antigen is linked to a virosome.

Within another aspect of the invention there is provided a second antigen comprising a modified polypeptide comprising three contiguous segments N, L and C represented by the formula N-L-C and comprising: a N-helix region of gp41(N), a C-helix region of gp41(C), and a connecting loop comprising a synthetic linker (L) between the N and C-helices, the linker replacing amino acids 593-617 of gp41, the numbering scheme being based upon the prototypic isolate HIV-1 HxB2 clade B strain, said polypeptide comprising the calveolin-1 neutralizing and 98.6 D epitopes, no 2F5 and 4E10 epitopes, no fusion peptide and has a minimal interleukin 2 (IL-2) immunogenic cross-reactivity.

Said second antigen according to the invention is hereinafter indifferently named "gp41 derived antigen" or "gp41 according to the invention" or "rgp41".

The second antigen according to the present invention almost maintain a native conformation of an interaction between the N- and C-helices and have the hydrophobicity that provides a soluble and stable trimeric form to said modified second antigen without substantially altering its immunogenic reactivity.

The 98.6D epitope is located in cluster II region of gp 41 and is recognized by the 98.6D human monoclonal antibody as described in Gorny M. K. et al., 1989, Proc. Natl. Acad. Sci., 86, pp 1624-1628 and Xu J.-Y. et al., 1991, J. Virol., 65, pp 4832-4838.

The calveolin-1 binding domain corresponds to the CBD1 peptide (SLEQIWNNMTWMQWDK, SEQ ID No. 8) in gp-41 (Benferhat et al., 2009, Mol. Immunol. 46 (4), pp 705-712). The fusion peptide corresponds to the amino-terminal region of gp41, which is exposed after formation of the coiled-coil form. This region is inserted into the membrane of the target cell, resulting in the fusion of virus and cell membranes; it corresponds to the region 512-539 of extracellular portion of gp 41 (Quintana et al., 2005, JCI; see FIG. 1).

According to the present invention, the second antigen allows the formation of rgp41-trimers and has retained the native gp41 antigenicity and presents a minimal IL-2 cross reactivity. Such cross reactivity can be determined by methods well known to the skilled man in the art such as gp41-ELISA and gp41-dot blot. An example of such a determination is presented below (see example 3, FIG. 2).

According to the present invention, the expression "retains the native gp41 antigenicity" or "without altering its immunogenic activity" means that a polypeptide according to the invention has almost the same level of antigenic and/or immunogenic activity as the wild type gp41.

The N and C segments which constitute the second antigen according to the present invention may be derived from any gp41 protein of HIV, including the HIV-1 and HIV2 strains, including laboratory strains and primary isolates. Preferably, these segments are derived from an HIV-1 strain, and in particular from an HIV1 HxB2 strain such as described in SEQ ID No. 1.

The nucleotide and peptide sequences of a large number of gp41 proteins are known and available, for example, on the Internet on the site hiv.lanl.gov and also in the corresponding Los Alamos compendia (HIV 35 Sequence Compendium 2005 Leitner T, Foley B, Hahn B, Marx P, McCutchan F, Mellors J, Wolinsky S, and Korber B, Eds., published by Theoretical Biology and Biophysics Group, Los Alamos National Laboratory, NM, LA-UR 06-0680).

Any sequence, as defined above and/or in the claims, into which one or more conservative mutations (which do not substantially modify immunogenicity) have been introduced is also covered by the above definition.

The amino acids are numbered with reference to the sequence of the gp41 protein described in FIG. 1 (which amino acid sequence is represented by SEQ ID No.1).

In a more preferred embodiment the second antigen of the invention is a sequence described by SEQ ID No. 17 or by SEQ ID No. 18.

In a further aspect of the invention, the second antigen also comprises at least one spacer peptide segment S. In a specific aspect, the second antigen of the invention is represented by SEQ ID No. 19 or SEQ ID No. 20, and respectively named Mo or M1.

Said spacer sequence being useful to obtain a better conjugation, e.g. linking of the polypeptide with a carrier, e.g. a virosome, rendering the reactive amino acids on which said grafting is done more accessible.

In particular it may allow to move further apart the amino-acid(s) on which said grafting is done from the membrane of the virosome.

The composition of said spacer segment, e.g. amino acid sequence can also be designed in order to help in the production process of a polypeptide according to the invention. In a particular embodiment of the invention, said spacer segment can comprise histidine residues that can participate to the purification step of the whole polypeptide (see below in example 1).

Said spacer peptide comprises at least the amino acid sequence described by SEQ ID No. 9, SEQ ID No. 10, SEQ ID No. 11 or SEQ ID No.12 at the C-terminal part of the polypeptide of the invention.

Said spacer sequence may also participate in the immunogenicity of a polypeptide according to the invention.

In preferred embodiments the N segment is represented by the amino acids 540-592 of gp41, the numbering scheme being based upon the prototypic isolate HIV-1 HxB2 and/or the C segment is represented the amino acids 618-664 of gp41 the numbering scheme being based upon the prototypic isolate HIV-1 HxB2.

According to a preferred embodiment, the N segment is the sequence described by SEQ ID No.13 or SEQ ID No. 14 and for the C segment is the sequence described by SEQ ID No.15.

In a still further aspect of the invention, said L fragment is a sequence described by SEQ ID No. 16.

The second antigen of the invention are able to form trimers.

In another aspect, the present invention deals with an aqueous composition comprising the second antigen of the invention, said second antigen forming a stable trimers in an aqueous medium The present invention, in particular as defined in the following claims, encompasses second antigen equivalent to those previously defined or described, in particular analogues thereof as defined.

Within the meaning of the invention, the expression "analogue thereof with respect to a gp41-derived antigen intends to refer to a peptide having substantial (at least 85%, in particular at least 90% and more particularly at least 95%) amino acid sequence identity or homology (i.e. amino acid residue replaced by an amino acid residue of the same family, of similar polarity or charge, for example) with the amino-acid sequence of said gp41-derived antigen, and which has similar or conserved biological properties, in particular with respect to the binding antigen portion of immunoglobulin directed against the gp41 protein.

The oligomeric, e.g. trimeric, state of a second antigen according to the invention can be determined by methods well known to those skilled in the art such a gel filtration for instance FPLC with a separation between 3000 and 600 000 Daltons.

The stability of the trimers formed by the second antigen of the invention can be measured by techniques well known to those skilled in the art such as several cycles of freeze and thawing of the aqueous composition comprising the second antigen of the invention.

The antigens according to the invention are obtained by any conventional or standard technique of chemical synthesis or of genetic engineering well known by the person skilled in the art.

According to one option, the antigens are produced by chemical synthesis: they may be synthesized in the form of a single sequence, or in the form of several sub-sequences which are then linked to one another. The chemical synthesis may be carried out in solid phase or in solution, these two synthesis techniques being well known to those skilled in the art. These techniques are in particular described by Atherton and Shepard in "Solid phase peptide synthesis" (IRL press Oxford, 1989) and by Houbenweyl in "Methoden der organischen Chemie" [Methods in Organic Chemistry] published by E. Wunsch Vol. 15-1 and 11, Stuttgart, 1974, and also in the following articles, which are entirely incorporated herein by way of reference: P. E. Dawson et al. (Science 1994; 266 (5186), pp 776-779); G G Kochendoerfer et al. (1999; 3 (6), pp 665-671); P E Dawson et al. (2000, 69, Annu. Rev. Biochem., pp 923-960).

According to another option, the antigens according to the invention are produced using genetic engineering techniques well known to those skilled in the art. When the said polypeptides according to the invention are produced by genetic engineering, they may comprise, at the NH2-terminal end, an additional methionine residue corresponding to the translation of the first initiation codon.

These techniques are described in detail in Molecular Cloning: a molecular manual, by Maniatis et al., Cold Spring Harbor, 1989. Conventionally, the PCR technique is used to produce the DNA sequence encoding the polypeptides according to the invention in a form which can be inserted into an expression vector. The expression vector containing the sequence of interest is then used to transform a host cell which allows for expression of the sequence of interest. The polypeptides produced are then isolated from the culture medium using conventional chromatography techniques well known to those skilled in the art. High performance liquid chromatography (HPLC) is preferably used in the purification stage. Typically, the cells are collected by centrifugation at the end of culture, and are taken up in a neutral buffer, in order to be disrupted by any suitable means. The cell lysate is then centrifuged in order to separate the soluble material from the insoluble material. SDS-PAGE analysis of the supernatant and of the pellet from centrifugation reveals whether the polypeptide is soluble or not. If the peptide is insoluble, solubilization is obtained using a buffer containing urea, guanidine or any other solubilizing agent. Centrifugation at this step makes it possible to remove debris and other insoluble products which would hamper the chromatography. The following step consists in loading the solubilized molecule onto an affinity column, which may be of the metal chelate type if a plurality of histidine residues such as in the linker segment L which can be integrated onto the polypeptide of interest. The system which enables the affinity purification may be varied in nature, such as immunoaffinity, affinity on cibachron blue, etc. At this stage, the polypeptide exhibits a degree of purity close to or greater than 80%, in particular of at least 90%, as may be determined by colorimetry of a SDS-PAGE electrophoresis followed by Coomassie blue staining. Densitometric measurement of the bands makes it possible to quantify the degree of purity. The degree of purity may also be measured by reverse-phase HPLC, by measuring the area of the various peaks. An additional chromatography step may be added in order to further purify the polypeptide; by way of example, mention may be made of gel filtration and reverse-phase chromatography.

In a further embodiment, the present invention also concerns a polynucleotide encoding the above defined polypeptides.

The polynucleotides of the present invention include both single-stranded and double-stranded DNA/RNA molecules.

In a specific aspect the present invention, a polynucleotide encoding a rgp41 according to the present invention is described by SEQ ID No.21 or SEQ ID No. 28.

Additional DNA sequences encoding modified polypeptides, remaining within the scope of the present invention, can be readily generated by those of ordinary skill in the art, based on the genetic code and the polypeptide sequences described in the present specification. Counterpart RNA sequences can be generated by substitution of U for T. Those skilled in the art will readily recognize that, in view of the degeneracy of the genetic code, sequence variation is possible among polynucleotide molecules coding for the polypeptides according to the present invention, in particular the polynucleotide sequences described in the present specification.

Conversely, any person skilled in the art will recognize that sequence variation is possible among polypeptides molecules encoded by the polynucleotides molecules according to the present invention, in particular the polynucleotide sequences described in the present specification, still in view of the degeneracy of the genetic code.

All these variations are encompassed by the invention definition(s) and appended claims, in so far that those variations do not substantially alter the structure/conformation, and/or function(s) and/or properties of the resulting polypeptide with reference to the ones specifically previously and/or hereinafter described.

According to one embodiment of the invention, a polynucleotide sequence according to the invention is directly chemically synthesized (Young L and Dong Q., 2004, -Nucleic Acids Res., April 15; 32 (7), Hoover, D. M. and Lubkowski, J. 2002, Nucleic Acids Res., 30, Villalobos A, et al., 2006. BMC Bioinformatics, June 6; 7:285).

The polynucleotide sequences of the invention thus obtained can be introduced in a known manner into any appropriate vector which makes it possible to express said polypeptide, optionally in modified form, in convenient cell systems.

The polynucleotide sequences thus obtained can be introduced into a host cell, so as to transform the host and promote expression (e.g. transcription and translation) of the introduced sequence. Vectors include plasmids, phages, etc. Use is preferably made of vectors in which the DNA sequence encoding a polypeptide according to the invention is under the control of a strong promoter, which may or may not be inducible. As an example of a promoter which may be used, mention is made of the T7 RNA polymerase promoter. The expression vectors may include a selectable marker, such as the ampicillin, tetracycline or other antibiotic resistance genes appropriate for use in humans. Alternatively the transformed cells can be selected thanks to an auxotrophic marker, or any kind of antibiotic-free selection means (complementation of an essential gene previously knocked-out into the host's genome).

Examples of expression vectors which may be used include the plasmids pET21b, pET30 (Novagen), yeast, bacteria, viral vectors, such as: baculoviruses, and poxviruses.

In order to promote the expression and purification of an antigen, according to the present invention, the latter may be expressed in a modified form, such as a fusion protein, and may include not only secretion signals, but also additional heterologous functional regions. For example, a region of additional amino acids, particularly charged amino acids, may be added at the N-terminal of the polypeptide in order to improve stability and persistence in the host cell.

An object of the invention also deals with an expression vector comprising a polynucleotide as described above.

Said vector can be used to transform a host organism, said host organism forming another object of the present invention.

The invention also provides a host cell transformed with said vector. Any host cell conventionally used in combination with the expression vectors described above may be used, for instance *E. coli*, BL21 (DE3), BLR (DE3), origami 2 (DE3), *Bacillus* or other gram positive hosts such as *Lactococcus lactis*, yeast, baculovirus and eukaryotic cells such as CHO or Vero. Preferred cell expression systems include *E. coli* such as BL21 (DE3).

In another of its aspect, the present invention deals with a conjugate, such conjugate comprises the second antigen according to the present invention.

An in a specific aspect, the second antigen the invention is conjugated with a virosome-like vesicle.

Virosome-Like Vesicle

A virosome-like vesicle suitable for the instant invention comprises at least virosomal lipids and preferably exhibits fusion membrane properties.

According to an embodiment, a virosome-like vesicle of the invention may comprise a unilamellar lipid bilayer.

According to an embodiment, a virosome-like vesicle of the invention may be a bi- or a multilamellar vesicle.

According to an embodiment, a virosome-like vesicle may have a diameter generally in the range of 50 to 600 nm, and in particular a diameter from 100 nm to 300 nm, and in particular from 200 nm to 400 nm.

Virosome-like vesicles of the invention may be spherical unilamellar vesicles with a mean diameter with approximately 150 nm. Virosome-like vesicles comprise, incorporated into the lipid bilayer, viral membrane proteins with or without fusion properties or fragments thereof.

The expression "fusion proteins or fragments thereof" is intended to refer to proteins or fragments thereof capable of inducing and/or promoting a fusion reaction between a virosome-like vesicle membrane and a biological membrane of the target cell.

For example, fusion proteins may be influenza membrane glycoproteins such as hemagglutinin (HA).

According to an embodiment, at least two different fusion proteins or fragments thereof may be used, that may display distinct fusion characteristic. According to another embodiment, distinct fusion characteristics may be, for example, different sensitivity to temperature, to ion concentration, to acidity, to cell type and to tissue type specificity.

According to an embodiment, a virosome-like vesicle may contain fusion proteins that mediate fusion at two distinct temperatures. According to another embodiment, hemagglutinin (HA) from different virus strains may be used to construct a virosome-like vesicle. As an example, HA molecules from both X-31 and PR8/34 virions may be capable of catalyzing two distinct fusion reactions at distinct temperatures.

Fusion proteins with different fusion characteristics may be derived from different influenza strains, or fusion proteins may be derived from other viruses, such as the vesicular stomatitis virus (VSV) EI protein, the Semliki Forest virus (SFV) envelope protein complex, or the Sendai virus F protein.

An antigen coupled to the membrane of a virosome-like vesicle may be degraded within the endosome and may be presented to the immune system by MHC class II receptors. An antigen contained within the lumen of a virosome can be delivered to the cytosol of an antigen-presenting cell by membrane fusion and degraded in the cytosol, after which it may be presented MHC Class I antigens. Cross-presentation of antigens delivered by virosomes may also occur.

Therefore, a virosome-like vesicle may be able to induce a humoral and/or a cellular immune response.

In particular, a virosome-like vesicle might induce the production of IgA antibodies, such as secretory IgA, as well as IgG or IgM. Protocols of preparation are well-known by the skilled person in the art. Suitable protocols for the preparation of virosomes are described, for example, in WO 2004/045582 or EP 0 538 437, EP 1 633 395, EP 1594466, which are incorporated herein by reference.

According to an embodiment, a virosome-like vesicle according to the invention may be obtained either from a virosome vesicle as such, or from a vesicle resulting from the fusion of a virosome vesicle with a liposome vesicle.

Preparation of virosome vesicles may be made by any known method of the skilled person in the art such as described by Stegmann et al., EMBO J. 6, 1987, no. 9, 2651-9, or de Jonge et al., Biochim. Biophys. Acta, 1758, 2006, 527-539, incorporated herein by reference. Virosome vesicles, for example, may be reconstituted from original viral membrane lipids and viral membrane glycoproteins after solubilization of, for example, intact influenza virus with octaethyleneglycol mono-N-dodecyl ether (OEG), sedimentation of the nucleocapsid (the viral glycoproteins and lipids will remain in the supernatant), and removal of the detergent from the supernatant with a hydrophobic resin (Bio-Beads SM2) (Stegmann T, et al., EMBO J. 6, 1987 2651-9).

Virosomes may also be reconstituted from original viral membranes by solubilizing viral membranes with a short-chain phospholipid, sedimentation of the nucleocapsid (only the viral membrane glycoproteins and lipids will remain in the supernatant), and removal of the short-chain lipid in the supernatant by dialysis.

After solubilization of the virus with a detergent or short-chain phospholipid, and the removal of the nucleocapsid as described above, antigens or adjuvants, solubilized in detergent or short-chain phospholipid may be added to the supernatant prior to the removal of the detergent or short-chain lipid, leading to incorporation of the antigen or adjuvant in the virosome so formed. Likewise, lipids solubilized in detergent or short-chain phospholipid, may be added to the supernatant for inclusion in the virosomal membrane. Preparation of virosome vesicles containing fusion proteins from different viruses may be performed by mixing supernatants containing solubilized viral membranes as described above, or by adding purified fusion proteins to such supernatant, before said removal of detergent or short-chain lipid.

According to one embodiment, a virosome-like vesicle according to the invention may be obtained from a fusion of a virosome vesicle with a liposome vesicle.

Therefore, according to one embodiment, a virosome-like vesicle of the invention may comprise virosomal and liposomal lipids. According to one embodiment, a virosome-like vesicle of the invention may comprise a lipid bilayer comprising lipids chosen from cationic lipids, synthetic lipids, glycolipids, phospholipids, glycerophospholipids, glycosphingolipids like galactosylceramid, sphingolipids, cholesterol and derivatives thereof.

Phospholipids may comprise in particular phosphatidylcholine, sphingomyelin, phosphatidylethanolamine, phosphatidylserine, phosphatidylglycerol, phosphatide acid, cardiolipin and phosphatidylinositol with varying fatty acyl compositions.

Cationic lipids may be chosen from DOTMA (N—[I-(2,3-dioleylaxy)propyl]-N,N,N-trimethylammonium chloride), DOTAP (N—[I-(2,3-dioleoyloxy)propyl]-N,N,N-trimethylammonium chloride, DODAC (N,N-dioleyl-N,N-dimethylammonium chloride), DDAB (didodecyldimethylammonium bromide) and stearylamine or other aliphatic amines and the like.

The lipids used in the invention may be formulated as small unilamellar liposomes in a mixture with DOPE (dioleoylphosphatidyl ethanolamine) that is widely used as helper lipid to facilitate disruption of the endosomal membrane.

According to another embodiment, co-emulsifying agent may be also used in order to improve the rigidity and/or the sealing of the vesicles. As an example of co-emulsifying agent, mention may be made of cholesterol and derivatives, as for example cholesterol ester charged or neutral as cholesterol sulphate; derivatives with a sterol backbone, for example derived from plants, such as phytosterol (sitosterol, sigmasterol); ceramides; and mixtures thereof.

Virosomes or their contents may be subject to hydrolysis and physical degradation upon storage. According to one embodiment, virosomes may be preserved for long-term storage by freeze-drying, and reconstituted with an aqueous solution before use. Lyoprotectants such as inulin may be added prior to lyophilization to help preserve virosome integrity during lyophilization and upon reconstitution (Wilschut, J. et al., J. Liposome Res. 17, 2007, 173-182). Preferably, spray freeze-drying is employed (Amorij, J. P. et al. Vaccine 17, 2007, 8707-17).

A virosome-like vesicle of the invention may further comprise a targeting moiety that target said vesicle to a specific cell or tissue.

According to one embodiment, a virosome-like vesicle of the invention may further comprise a targeting moiety that target said vesicle to a specific cell or tissue.

A suitable targeting moiety may be chosen from a cell-surface receptor, a chemokine, a cytokine, a growth-factor, an antibody or an antibody fragment, a peptide sequence with specificity or specific charge complementary to an adhesion molecule such as an integrin. A targeting moiety may be incorporated into, or attached to the lipid bilayer of said vesicle, by any known techniques of the skilled person in the art.

According to one embodiment, the antigen located to the external surface of virosome-like vesicle of the invention may be:

- Covalently linked with a lipid of said virosome-like vesicle, or
- Intercalated into a lipid bilayer of said virosome-like vesicle by a peptide transmembrane domain.

According to one embodiment, the antigen may be contained within the virosome.

Modifications of the antigen of the invention and methods for cross-linking said modified antigen to the external surface of a virosome-like vesicle may be as those described in WO 2004/078099.

According to one embodiment, the antigen may be covalently linked to the external surface of a virosome-like vesicle by cross-linking with a lipid or a phospholipid. According to another embodiment, the antigen may be covalently linked to the external surface of a virosome-like vesicle by cross-linking with a carbohydrate. According to an embodiment, a covalently linked antigen may comprise at least one C-terminally positioned cross-linking residue.

For example, cross-linking residue may be chosen from cysteine (Cys) or lysine (Lys). According to another embodiment a covalently linked antigen may further comprise at least one spacer residue between said C-terminally positioned cross-linking residues and a corresponding C-terminal antigen extremity.

A suitable spacer residue may be chosen, for example, from Gly (glycine), Ala (alanine), Ser (serine), Asp (aspartate), Lys (lysine), Gln (glutamine), His (histidine), He (isoleucine) and Leu (leucine) residues. From 2 to 12, in particular from 3 to 10, and more particularly from 4 to 8, spacer residues may be linked to form spacer sequences. Suitable spacer sequences may be chosen, for example, from Gly-Gly or Lys-Gly.

Cross-linking of the antigen to the surface of a virosome-like vesicle may be, for example, performed by the use of amphiphilic PEG derivatives, a phosphatidylethanolamine (PE), a phosphatidylcholine (PC), a phosphatidylserine, a cholesterol, or a mixture thereof, readily incorporated into lipids bilayer. Cross-linking of the antigen to a lipid of a virosome-like vesicle of the invention may be performed by any method known to those skilled in the art.

The cross-linking may be operated in a lipid solution and the lipid-peptide conjugate may be subsequently incorporated into a virosome-like vesicle.

According to an embodiment of the invention, the antigen may be linked to a lipid of a vesicle of the invention, for example, by a bifunctional succinate linker, in particular a [gamma]-maleinidobutyric acid N-hydroxysuccinimide ester or a N-[gamma]-maleimidobutyryloxy-succinimide-ester.

Antigens, lipid linked antigens, phospholipids and adjuvants may be added to the supernatant formed after solubilization of a virus with a detergent or short-chain phospholipid, and the removal of the nucleocapsid as described above. Virosomes may be then formed, as previously described, by detergent removal for example using Bio-Beads SM-2 (Biorad), Amberlyte XM, or short-chain phospholipid may be removed by dialysis.

Adjuvants

According to an embodiment, the immunostimulatory effect of virosome-like vesicles of the invention may be further increased by associating those virosome-like vesicles with at least one adjuvant.

Said adjuvant may be encapsulated inside and/or incorporated in the lipid bilayer of, and/or freely combined with said vesicle.

According to one embodiment, a virosome-like vesicle may additionally comprise at least one adjuvant enhancing and/or mediating an immune response chosen from an innate immune response and/or an adaptative immune response. Usable adjuvants may enhance the immunological response by activating antigen presenting cells (APC), macrophages and/or stimulating specific sets of lymphocytes.

An adjuvant that may convene to the instant invention may be any ligand suitable for the activation of a pathogen recognition receptor (PRR) expressed in and on dentritic cells (DCs), T-cells, B-cells or other antigen presenting cells.

Ligands activating the nucleotide-binding oligomerization domain (NOD) receptor pathway may be suited for the purpose of the invention. Adjuvants suitable for these ligands may be muramyl dipeptide derivatives. Ligands activating the Toll-like receptors (TLRs) may also convene for the purpose of the invention. Those receptors are member of the PRR family and are widely expressed on a variety of innate immune cells, including DCs, macrophages, mast cells and neutrophils.

As example of ligands activating TLR, mention may be made, for TLR4 of monophosphoryl lipid A, 3-O-deacytylated monophosphoryl lipid A, LPS from *E. coli*, taxol, RSV fusion protein, and host heat shock proteins 60 and 70, for TLR2 of lipopeptides such as N-palmitoyl-S-2,3(bispalmitoyloxy)-propyl-cysteinyl-seryl-(lysil)$_3$-lysine, peptidoglycan of *Staphylococcus aureus*, lipoproteins from *M. tuberculosis, Sacharomyces cerevisiae* zymosan, and highly purified *P. gingivalis* LPS, for TLR3 of dsRNA, for TLR5 of flagellin, for TLR7 synthetic compounds such as imidazoquinolines or for TLR9 of certain types of CpG-rich DNA. Other useful adjuvants for the invention may be T helper epitopes.

A T helper epitope is a peptide usually derived from exogenous proteins that have undergone proteolytic degradation and processing within the endocytic pathway of antigen presenting cells (APCs). In those cells the Major Histocompatibility Complex of class II (MHC II) associates with those peptides in endosomes. This complex transported to the surface of the APCs may interact with a specific T cell receptor of T lymphocytes CD4 leading to their activation. According to the helper epitope, the T cell response may be of Th1 and/or Th2 type, as known in the art.

As an example of a Th-oriented response epitope one may mention pan DR helper T cell epitope (PADRE). This epitope is engineered to bind most common HLA-DR molecules with high affinity and to act as a powerful immunogen. The PADRE HTL epitope has been shown to augment the potency of vaccines designed to stimulate a cellular immune response (Alexander J. et al., Immunol Res. 18, 1998, 79-92).

According to an embodiment, an adjuvant that may be used with the virosome-like vesicles of the present invention may be chosen from aluminum salts, aluminum phosphate gels, mycobacteria such as BCG, *M. Vaccae*, or *corynebacterium parvum*, peptides, keyhole limpet hemocyanin, interleukin-2 (IL-2), IL-12, GM-CSF, ligands from the chemokine family, such as RANTES (Regulated upon Activation Normal T cell Expressed and Secreted), a lipoprotein of Gram bacteria, a yeast cell wall component, a double-stranded RNA, a lipopolysaccharide of Gram<"> bacteria, flagellin, a U-rich single-stranded viral RNA, a CpG containing DNA, a Suppressor 6f Cytokine Signalling small interfering RNA (SOCS siRNA), mellitin derived peptides, a pan DR epitope (PADRE) and mixtures thereof.

Such preparations may routinely contain pharmaceutically acceptable concentrations of salt, buffering agents, antioxidants, preservatives, compatible carriers, adjuvants as previously described and optionally other therapeutic agents.

Virosome-like vesicles of the invention, and in particular compositions comprising thereof may be administered by injection or by a mucosal route, or a combination thereof.

Injection routes may be, for example, intraperitoneal, intradermal, subcutaneous intravascular or intramuscular route.

Any mucosal route may be used, such as the genito-urinary route or for example vaginal route, gastro-intestinal route, the anorectal route, respiratory route, application to the upper mucosal tissue, the mouth-nasal route and mixtures thereof.

In one embodiment, the first and or second antigen of the invention may be provided as oral dosage forms, such as tablets, capsules (each including timed release and sustained release formulations), pills, powders, granules, elixirs, tinctures, solutions, suspensions, syrups and emulsions.

According to the present invention, said first antigen and said second antigens of the invention can be co-administered to a same patient, in a same dosage or in respectively different dosages according to the method of the present invention.

In a particular embodiment said co-administration of said first and second antigens can be done by at least two different routes, at a same time or at respectively different or following times.

In a further embodiment, the invention comprises co-administering, said first and second antigens, by a systemic route, such as injection, for instance intramuscular route, and a topic route, such as through mucosal epithelium, for instance through intranasal inhalation.

Said co-administration to a same patient of said first and second antigen, can be made by the same route, for instance systemic route, at the same time or respectively different or following times.

The prophylactic method of the invention, for performs in vivo at least one of the following functions:

a) Inducing innate or adaptative immunological response such as systemic and/or mucosal antibodies containing IgA and/or IgG isotypes, against HIV-1;

b) Controlling and/or deleting the viremia of a patient infected by HIV-1;

c) Blocking or reducing the HIV virus entry across a mucosal epithelium;

d) Preventing or reducing primary HIV infection in the lamina propria underneath a mucosal epithelium;

e) Preventing or reducing virus migration in the gut and to lymph nodes;

f) Preventing or reducing HIV infection in lymph nodes;

g) Triggering a mucosal immune response against HIV-1 in the genital and intestinal compartments;

h) Promoting systemic and mucosal immunes responses against HIV;

i) Controlling HIV infection, such as obtaining delayed, transient, or inferior infection;

j) Preventing HIV transcytosis;

k) Neutralizing HIV infection in vivo.

l) Inducing an antibody-dependant cellular cytotoxicity.

Within the meaning of the invention, the expression "adaptative immune response" is intended to refer to an immune response relying upon the activation of the immune system component implying specificity and memory with respect to an antigen or a pathogen.

Such a response may be highly specific toward an antigen or a pathogen and is more effective on second and subsequent encounter, with the antigen or pathogen. Such adaptative immune response may rely on the activation of lymphocytes, such as T-cells or B-cells.

Within the meaning of the invention, the expression "innate immune response" is intended to refer to a response relying upon non-specific recognition system and does not alter upon subsequent encounter with the antigen or pathogen.

Such system may rely upon immune cells such as, for example, monocytes macrophages or natural killer (NK) cells or natural killer T (NKT) cells.

In another aspect the invention deals with a kit for implementing a therapeutic method as described above, comprising said first and second antigen.

The present invention also deals with a therapeutic composition or preparation comprising a first antigen and a second antigen as described above.

Within a specific aspect, said first antigen and said second antigen are in the same dosage or in respectively different dosages or dosage forms.

The present invention deals in a still further embodiment with a therapeutic, in particular, a prophylactic vaccinal association associating:

- a first medicament comprising a first antigen as defined above, and
- a second medicament comprising a second antigen as defined above.

The instant invention will be further understood with the following examples which are presented for illustrating purposes and should not be interpreted as limiting the scope of the instant invention.

Figure 1:
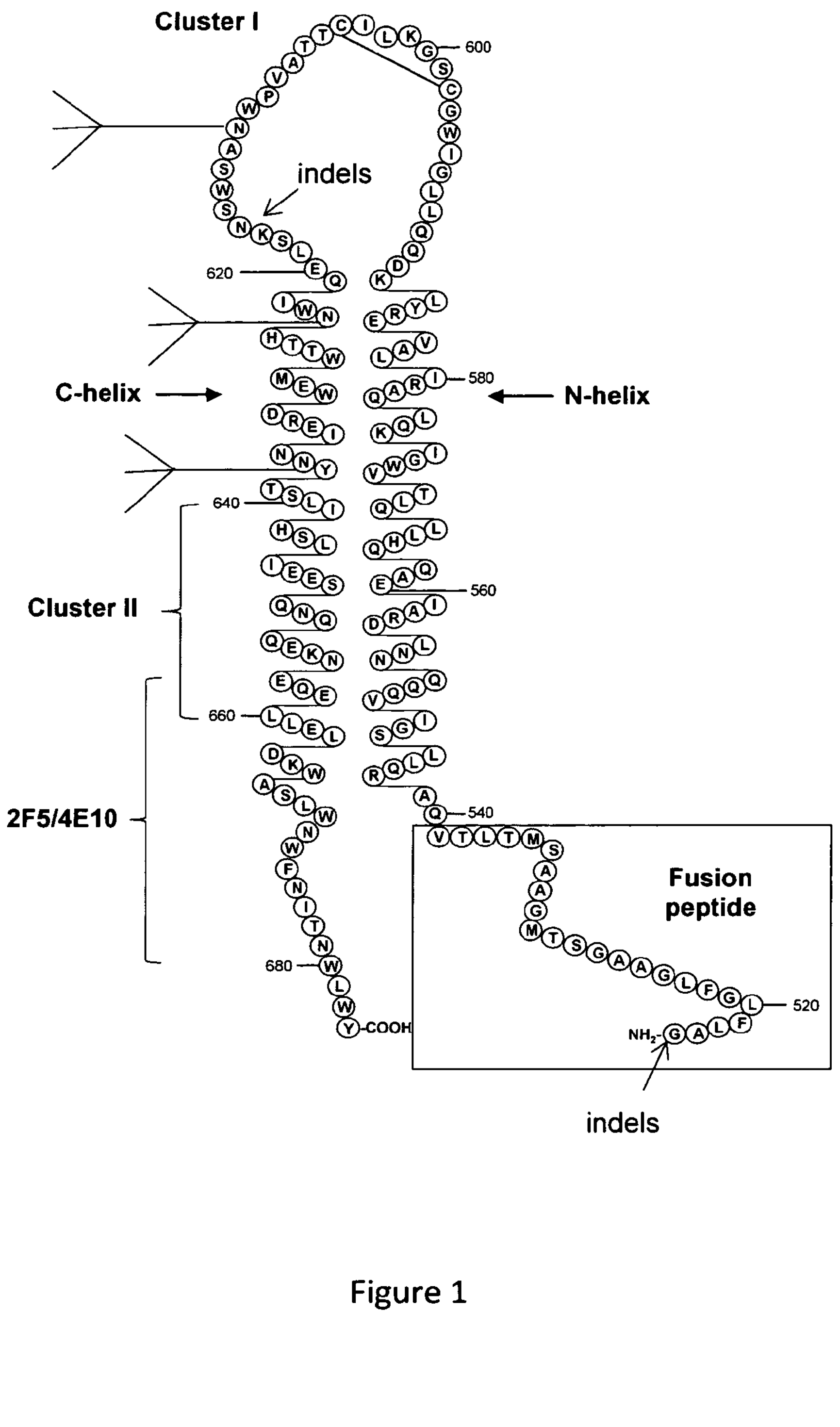
FIG. 1: Diagram of the structure of the HIV-1 envelope glycoprotein gp41 of clade B, HxB2 strain (SEQ ID No. 39), presenting the well known epitopes, clusters and regions identified. Open circles correspond to invariant amino acids, light gray circles correspond to highly conserved amino acids, middle gray circles correspond to moderately variable amino acids, dark circles correspond to invariant amino acids and amino acids that are significantly more variable in one clade than another, are figured as heavily outlined circles. Part of the MPER region, containing the epitopes for the broadly neutralizing antibodies 2F5 and 4E10, and present in the PI peptide of the present invention, is shown on the lower left; this part is absent from the gp41 polypeptide of the invention. Amino acids from cluster 1 are replaced by a linker in the gp41 protein constructs of the invention.

Panel B: Viremia in monkeys vaccinated with virosomes gp41-derived antigens from clade B (Group 3 of example 6) and challenged with SHIV clade C, with strain SHIV1157ipd3N4. Eighteen months after the fourth vaccination, animals received a boost and five week later they were challenged intravaginally 10 times with 10-20 $TCID_{50}$. The plasma viral load is indicated by the lines for individual animals; note the detection limit is $10^3$ copies per ml.

EXAMPLES

Example 1

Construction of M0 and M1, Polypeptide of the Invention (rgp41) Encoded by SEQ ID No. 28 and SEQ ID NO 21 by Molecular Biology a) First Step: Construction of gp41-dloop (SEQ ID No.27)

The gp41-delta loop was constructed by PCR.

Design of the Primers

The oligonucleotide primer gp41-Nde (SEQ ID No.22) and the oligonucleotide primer gp41-Bam1 (SEQ ID No.23) were used to amplify the N-helix and introduce the hydrophilic linker). These oligonucleotide primers were designed to respectively introduce the sites for restriction enzymes NdeI and BamHI. The oligonucleotide primer gp41-Bam1 was also designed to introduce the oligopeptide linker SGGRGGS (SEQ ID No.16) to replace the deleted portion of loop.

The oligonucleotide primer gp41-Bam2 (SEQ ID No.24) and the oligonucleotide primer gp41-XhoI (SEQ ID No.25) were used to amplify the C-helix of gp41 by PCR. Those oligonucleotide primers were designed to introduce the BamHI and the Xho1 enzyme restrictions sites, respectively.

Conditions of PCR

The gp41dloop polynucleotide was amplified from the gp41 matrix (SEQ ID No.26) by PCR using the above-described oligonucleotide primers. Plasmid was used at 0.5 μg/μl, primers were used at 10 μM each, and dNTP were used at 10 mM each. The amplification was conducted using the DNA polymerase DyNazyme from Finnzymes. The amplification was initiated with a denaturing step of 5 minutes at 94° C., following by 30 cycles, each comprising a one minute step at 94° C. (denaturing step), a one minute step at 60 C ° (hybridization), and a one minute step at 72° C. (elongation), and the amplification was terminated by a last step of 10 minutes at 72° C. The purified PCR products were digested by NdeI (Ozyme, R0111S) and XhoI (Ozyme, R0146S) for insertion in pET21b. The pET21b vector (Novagen) digested by NdeI and XhoI and the PCR products were extracted and purified. Ligation was made using Quick ligation kit (New England Biolabs) according to the manufacturer prescription resulting in pET21b-gp41dloop.

pET21b-gp41dloop products were transformed in DH5-alpha (Invitrogen).

b) Second Step: Construction of M0gp41C-dloop Clade B (SEQ ID No.28) Encoding M0 Polypeptide (rgp41 According to the Invention)

Two PCRs were performed on the matrix GP41dloop (SEQ ID No.27) to obtain the M0gp41C_CladeB construct using the Phusion polymerase (Finnzymes). The first reaction was carried out with the primers: GP41B-C-D1 (SEQ ID No. 29) and GP41B-C-R2 (SEQ ID No. 30)

The second reaction was performed with the primers: GP41B-C-D1 (SEQ ID No. 29) and GP41B-C-R1 (SEQ ID No. 31).

The positive PCR products were digested using NdeI (Ozyme, R0111S) and XhoI (Ozyme, R0146S) restriction enzymes for the insertion of the Gp41C_CladeB encoding gene into pET30b (VWR, 69910-3). The pET30b vector was digested using NdeI and XhoI restriction enzymes (Ozyme). The DNA fragments corresponding to Gp41C_CladeB gene and pET30b were extracted and purified (using extraction kit from Macherey-Nagel, 740 609 250). Ligation of these two fragments was done using the Quick ligation kit (New Englands Biolabs Inc, M2200S). 1 μl of the ligation mixture was used to transform *E. coli* DH5-alpha (Invitrogen, 12297-016). Transformants were isolated on LB Agar plates with 30 μg/mL kanamycin. Isolated colonies were inoculated in 4 mL of LB medium supplemented with 30 μg/mL kanamycin. Cultures were performed overnight at 37° C. and 180 rpm. DNA extraction from the corresponding pellets was performed according to the protocol given in the Nucleospin Plasmid extraction kit from Macherey-Nagel, Ref. 740588-250. They were analyzed by restriction enzyme digestion and the inserts were sequenced using T7prom (SEQ ID No. 32) and T7term (SEQ ID No.33) primers.

The complete nucleotide sequence of M0gp41dloop-C CladeB was determined and is represented by SEQ ID No. 28 c) Third step: construction of M1gp41C-dloop Clade B (SEQ ID No. 21) Encoding M1 Polypeptide (rgp41 According to the Invention)

The M1gp41C-dloop clade B was constructed by PCR. Two PCRs were performed on the matrix Gp41dloopC_CladeB (SEQ ID No. 28) to obtain M1gp41C-dloop clade B. using the Phusion polymerase (Finnzymes).

The first reaction was done with the primers: GP41B-C-D1 (SEQ ID No. 29) and GP41-C3-R1 (SEQ ID No. 34).

Before the second PCR reaction, purification was done using the nucleospin extract kit (Macherey Nagel, 740609250) with the following primers: GP41B-C-D1 (SEQ ID No. 29) and GP41-C3-R2 (SEQ ID No.35).

The positive PCR products were digested using NdeI (Ozyme, R0111S) and XhoI (Ozyme, R0146S) restriction enzymes for the insertion of the M1gp41dloop-C CladeB encoding gene into pET30b (VWR, 69910-3). The pET30b vector was digested using NdeI and XhoI restriction enzymes (Ozyme). The DNA fragments corresponding to M1gp41dloop-C CladeB gene and pET30b were extracted and purified (using extraction kit from Macherey-Nagel, 740 609 250). Ligation of these two fragments was done using Quick ligation kit (New Englands Biolabs Inc, M2200S). 1 μl of the ligation mixture was used to transform *E. coli* DH5-alpha (Invitrogen, 12297-016). Transformants were isolated on LB Agar plates with 30 μg/mL kanamycin. Isolated colonies were inoculated in 4 mL of LB medium supplemented with 30 μg/mL kanamycin. Cultures were performed overnight at 37° C. and 180 rpm. DNA extraction from the corresponding pellets was performed according to the protocol given in the Nucleospin Plasmid extraction kit from Macherey-Nagel, Ref. 740588-250. They were analyzed by restriction enzyme digestion and the inserts were sequenced using T7prom (SEQ ID No.32) and T7term (SEQ ID No.33) primers.

The complete nucleotide sequence of M1gp41dloop-C CladeB was determined and is represented by SEQ ID No.21.

Example 2

Modified Polypeptide Reproduction in *E. coli* a) Transformation pET30b-M0gp41dloop-C Clade B or pET30b-M1gp41dloop-C Clade B plasmid was transformed in the expression *E. coli* strain BLR (DE3). The expression of M1gp41dloop-C and M0gp41dloop-C Clade B was driven by a T7 promoter.

b) Expression tests Six cultures of *E. coli* strain BLR (DE3) carrying the pET30b-M1gp41dloop-C CladeB or pET30b-M0gp41dloop-C Clade B plasmid were grown at 37° C. in Luria Broth with 30 μg/ml kanamycin until the optical density at 600 nm reached 0.6 (spectrophotometer Jasco V-530). The modified polypeptide was induced with 1 mM IPTG (isopropyl BD-thiogalactoside), and the culture continued for further 2 hours at 37° C. Expression of proteins was checked by separation on SDS-4-12% PAGE.

c) Production

1) Culture One liter of culture of BL21 (DE3)/pET30b-M1gp41dloop-C CladeB or (DE3)/pET30b-M0gp41dloop-C CladeB was grown in Luria Broth at 37° C. until the optical density at 600 nm reached the value of 6.0. The expression of gp41-engineered loop was induced by 1 mM IPTG, and the culture continued for a further 2 hours at 37° C. The culture was centrifuged (Centrifuge Beckman Coulter Avanti J20XP with rotor JLA 8-1000, 4000×g, 30 min, 4° C.) and the pellet was stored at −80° C.

2) Extraction of M0 or M1 rgp41 Modified Polypeptides

The pellet was resuspended with a sonication buffer (40 mL of Tris-HCl 50 mM pH8, NaCl 300 mM). Bacteria were disrupted by a 15 min sonication step on ice/ethanol (disintegrator UP200S amplitude 80%, coefficient 0.5). Then the suspension was centrifuged at 40 000×g during 30 min at 4° C. to separate the soluble proteins (supernatant) from the insoluble proteins (pellet) (Centrifuge Beckman Coulter Avanti J20XP with rotor JA20).

d) Purification of M1 rgp41 Modified Polypeptide

1) Affinity Chromatography

A first step of purification of M1 (encoded by M1gp41dloop-C CladeB, SEQ ID No. 21) was performed by affinity chromatography on Ni Sepharose™ 6 Fast Flow media packed into a XK16/20 column (GE Healthcare) with a column volume of 1 mL of medium per 1 L of culture in flasks. The specific spacer peptide S allowed the use of an affinity chromatography step as capture step to recover the soluble fraction of M0 or M1. This was relevant because of the low productivity of the protein. The column was equilibrated with a buffer Na-Phosphate 50 mM pH7.5, NaCl 300 mM, β-mercaptoethanol 5 mM. Clarified samples of M1 peptide in Na-Phosphate 50 mM pH7.5, NaCl 300 mM, β-mercaptoethanol 5 mM, $MgCl_2$ 2 mM, Leupeptine and Pepstatine 0.1 mM was loaded onto the column at 2 ml/min. The column was then washed with equilibration buffer and elution steps at 25 mM, 50 mM and 150 mM Imidazole. M1 gp41 was eluted with a buffer Na-Phosphate 50 mM pH7.5, NaCl-300 mM, β-mercaptoethanol 5 mM, Imidazole 300 mM at 4 mL/min. Tween®20 at a final concentration of 0.05% was added on pooled fraction affinity chromatography and a dialysis was performed overnight at 4° C. under slow magnetic agitation against buffer Na-Phosphate 50 mM pH7.5, NaCl 300 mM, TCEP 1 mM, Tween20 0.05%. Samples were then concentrated 3 times by centrifugation on an Amicon 10 kDa concentration unit (Millipore).

2) Size Exclusion Chromatography A second purification step of M1 was performed by Size Exclusion Chromatography using Superdex™ 200 Prep grade media packed into a XK26/60 column (GE Healthcare) with a column volume of 320 ml. The column was equilibrated with a buffer Na-Phosphate 50 mM pH7.5, NaCl 300 mM, TCEP 1 mM, Tween20 0.05%. M1 in Na-Phosphate 50 mM pH7.5, NaCl 300 mM, TCEP 1 mM, Tween20 0.05% was loaded onto the column at 1.5 ml/min and eluted with the equilibration buffer at 2.5 mL/min. According to the calibration curve the protein was eluted as soluble trimers. Therefore, the presence of the spacer comprising the cysteine residue at the C-terminal part of M1 or M0 does not modify the conformational state of the protein.

Example 3

Cross Reactivity

Figure 2:
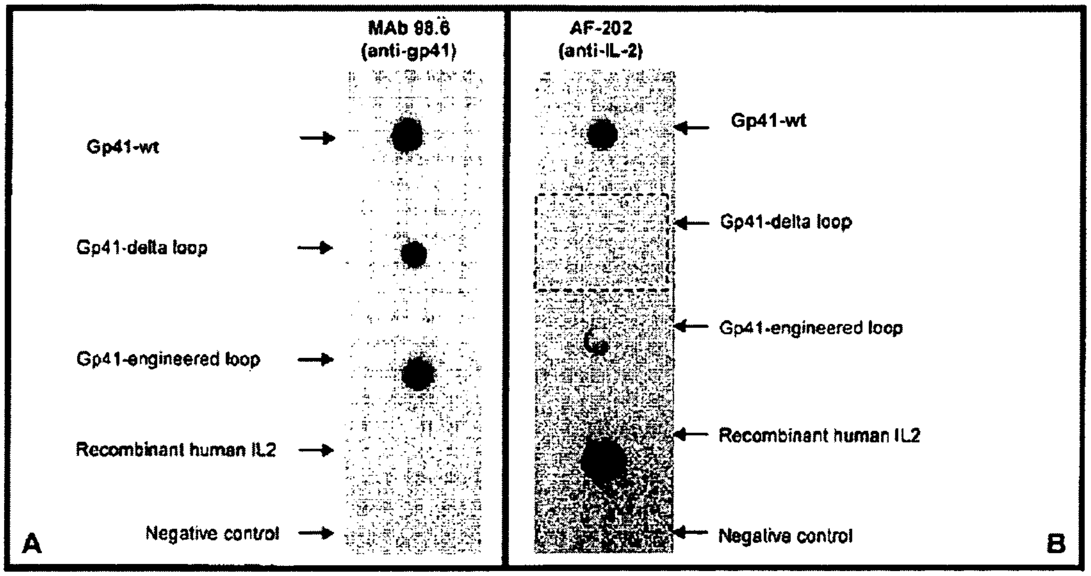
FIG. 2: cross reactivity of wild type gp41 and derivatives with a monoclonal antibody against gp41, MAb 98.6 (left) and an anti-IL2 antibody, AF-202 (right).

Four proteins were spotted on a nitrocellulose membrane: wt gp41-HA (the native gp41 fused to an HA tag (GenBank AF348176) in Tris 50 mM pH 8, NaCl 200 mM, Triton X-100 0.1%, 0.1 mg/ml, Gp41-delta loop (SEQ ID No. 38) which differs from the native gp41 fragment of FIG. 1 mostly by the replacement of 25 residues in cluster I with the linker of SEQ ID No. 16 in Tris 50 mM pH 8, NaCl 200 mM, glycerol 5%, 0.2 mg/ml, Gp41-engineered loop (SEQ ID No.37), which differs from the native gp41 fragment of FIG. 1 mostly by replacement of 12 residues in cluster I with the linker of SEQ ID No 16) in Tris 50 mM pH 8, NaCl 200 mM, Imidazol 200 mM, glycerol 5%, 0.2 mg/ml, human recombinant IL-2 in Tris 50 mM pH 8, NaCl 200 mM, 0.1 mg/ml and a negative control (bovine serum albumin), (FIG. 2).

The membrane was incubated at 37° C., and then put in 20 ml of PBS Tween 0.3%, 5% milk for one additional hour under agitation. The 98.6 D (an anti-GP41 human monoclonal antibody from NIBSC, UK) and AF-202 (an anti-human-IL-2 antibody from R & D systems) antibodies were added at a final concentration of 0.05 μg/ml or 0.5 μg/ml respectively, in 20 ml of PBS/Tween 20 0.3%-5% milk for one hour with agitation. An appropriate concentration of anti-IgG peroxidase coupled antibody was added in 20 ml of PBS Tween 0.3%, milk 5% with agitation for one hour, and the blot was washed three times for 15 minutes each in PBS Tween 0.3%. The two peroxidase activity was then revealed with a commercial enhanced chemiluminescence kit (Amersham) and a Kodak film was exposed to the blot, as known in the art.

As shown in FIG. 2, the native Gp41 is strongly recognized by the anti-human IL-2 antibody, the replacement of 25 residues in cluster I has abolished the recognition of this protein by the human anti-IL-2 antibody, the replacement of 12 residues in cluster I partially abrogated the reactivity by the human anti-IL-2 antibody, the recombinant human IL-2 is as expected strongly recognized by the AF-202 anti-IL-2 antibody. However, replacement of the 12 or 25 amino acids by a linker does not affect recognition by the anti-gp41 monoclonal antibody 98.6.

Example 4

Solubility Test of the rgp41 Polypeptide

Cultures of *E. coli* expressing the gp41 polypeptide according to the invention were centrifuged at 4 000 g at 4° C. during 15 min. Pellets were suspended in a volume of lysis buffer: phosphate 50 mM pH 7.5, NaCl 300 mM, MgCl2 2 mM, beta-mercaptoethanol 5 mM, benzonase 1 microM, pepstatine 1 microM, leupeptine 1 microM to reach OD 600 nm=10. The solution was incubated at 4° C. for 30 minutes.

Cell lysis was performed by three cycles of freezing/thawing. Soluble and insoluble proteins were separated by a 30 min centrifugation at 21 000 g at 4° C. Ten microliters of proteins were analyzed to determine the expression and solubility level by SDS-PAGE 4-12% electrophoresis followed by Coomassie blue staining. The rgp41 polypeptide was found to be present in the supernatant. Therefore, the protein is soluble.

Example 5

Preparation of Virosome-Like Vesicles Presenting a gp41 Polypeptide Produced in *E. coli* on the External Surface (rgp41-Virosomes), and Preparation of Virosomes Presenting a Synthetic Peptide on the External Surface (P1-virosomes)

Virosome-like vesicles were prepared essentially as as described in WO 2007/099387. Briefly, influenza A/Singapore/6/86 virus was grown in embryonated eggs and inactivated with beta-propiolacton as known in the art. The virus was dissolved in 100 mM of octaethyleneglycolmonodecylether (OEG) in phosphate buffered saline (PBS), and the viral nucleocapsid removed by ultracentrifugation. The solubilized membranes, containing 4 mg of hemagglutinin, were mixed with 32 mg egg phosphatidylcholine (PC) and 8 mg of phosphatidylethanolamine (PE) dissolved in 2 ml of PBS containing 100 mM OEG. The phospholipids and the hemagglutinin containing solution as described above were mixed and sonicated for 1 min. This solution was centrifuged for 1 hour at 100 000 g and the viral membrane preparation/lipid mixture was sterilized by filtration.

A polypeptide of the present invention, comprising a spacer and a cysteine residue at the C-terminal position (SEQ ID NO 19) was conjugated through a maleimido-succinimide linker at the N-terminus to a regioisomer of phosphatidylethanolamine (PE) as follows.

Phosphatidylethanolamine (PE) was dissolved in methanol and 0.1% (v/v) triethylamine was added. The solution was then mixed with the heterobifunctional cross-linker N-[gamma]-maleimidobutyryloxy-succinimide-ester (GMBS), (Pierce Chemical Company, Rockford, Ill.) (ratio PE:GMBS=5:1) which was previously dissolved in dimethylsulfoxide (DMSO) (20 μl). After incubation for 30 minutes at room temperature, the solvents were evaporated for 1 h under vacuum in a speedvac centrifuge. The GMBS-PE was then dissolved in 1 ml of PBS containing 100 mM octaethyleneglycol (OEG) (Fluka Chemicals, Switzerland), (PBS-OEG) and the polypeptide of the present invention comprising segment S with a cysteine residue at the C-terminal position (SEQ ID NO 19), was added (ratio PE-GMBS: polypeptide=5:1). At this step, the maleimide of the phosphatidylethanolamine-GMBS reacts with the sulfhydryl of the free C-terminal cystein of the gp41 polypeptide. After in incubation time of 30 minutes, excess free cystein was added, in order to quench any remaining free GMBS (ratio Cystein: GMBS=10:1).

The lipid-conjugated polypeptide was added to the hemagglutinin-containing viral membrane preparation/lipid mixture as described above at a ratio of 1 mg of rgp41 per mg of hemagglutinin, and rgp41-virosomes were formed by detergent removal on SM-2 BioBeads (BioRad, Glattbrugg, Switzerland).

Likewise, the lipid-linked synthetic peptide PI which aminoacid sequence corresponds to SEQ ID No. 5 (SQTQQGKNEQELLELDKWASLWNWFDIT-NWLWYIKLSC (carboxymethyl(1,3-dipalmityol-glycero-2-phophatidylethanolamino))-OH was synthesized as the TFA salt SQTQQGKNEQELLELDKWASLWNWFDIT-NWLWYIKLS-hydroxylcysteine (SEQ ID No. 40) by solid-phase Fmoc chemistry as known in the art, and linked to phosphatidylethanolamine via its C-terminal hydroxylcysteine using bromoacetyl-phosphoshatidylethanolamine. After purification by preparative HPLC, and ion exchange to produce its acetate salt, the peptide was lyophilized, dissolved in PBS-OEG was mixed with the viral membrane preparation/lipid mixture, at a ratio of 5 mg PI per mg of viral hemagglutinin, and PI-virosomes were formed by detergent removal.

Example 6

Immunization of Macaques with a Vaccine Composition Comprising rgp41-Virosome Like Vesicles of the Invention and P1-Virosomes of the Invention Immunization of macaques with a vaccine composition comprising virosome-like vesicles with rgp41 polypeptide as described above as well as virosome-like vesicles with gp41 derived antigen peptide P1 located at the external surface was carried out as follows.

Three groups of 5 female macaques with an average age of about 5 years were used. Four weeks before the first administration of vaccine, all macaques received intramuscular injections of beta-propiolacton inactivated influenza A Singapore 6/86 (100 μl, 0.01 mg/ml). Thereafter, macaque vaccinations with virosome-like vesicles in aqueous solution (40 μg of P1-virosomes and 40 μg of rgp41-virosomes, 100 μl) were carried out in week 0, 7, 15 and 24. Group 1 (monkeys G1.1 to G1.6) received influenza virosomes without gp41 antigens (placebo). Group 2 (G2.1-2.6) received four intramuscular vaccinations with both P1-virosomes and gp41-virosomes at every vaccination, and group 3 (G3.1-3.6) two intramuscular vaccinations (week 0 and 7) followed by two intranasal vaccinations (week 15 and 24), administered as a spray, each time with both P1-virosomes and gp41-virosomes. One animal in group 3 (3.2) died for reasons unrelated to vaccination.

Serum samples were taken at each vaccination time point.

The level of total IgG and IgA antibodies in serum was determined according to the following ELISA protocol. Peptide P1 (SEQ ID NO 5) 100 ng/100 μl/wells, or rgp41 of the invention (SEQ ID No. 19, 100 ng/100 μl/well) in a bicarbonate buffer 50 mM, pH 9.6 was used to coat ELISA plates (Nunc) overnight at 4° C. Plates were saturated with BSA 2% PBS Tween 0.1% for 1 hour 37° C., then washed with PBS-Tween 0.1% buffer. Serums diluted 1/300 for IgA or 1/200 for IgG with PBS Tween 0.1% were incubated overnight at 4° C. Plates were thereafter rinsed with PBS-Tween 0.1% buffer. For detection of macaque IgG, an anti-macaque IgG goat antibody couple to biotin (Rockland) (1/15 000) was used followed with an incubation with streptavidine-HRP (Immunotech) diluted 1/50 000.

For the detection of macaque IgA, an anti-macaque IgA goat antibody coupled to biotin (Rockland) 1/15 000) was used followed with an incubation with streptavidine-HRP (immunotech) diluted 1/50 000.

A 2F5-IgA monoclonal antibody was used as positive control, followed with an incubation with an anti-human IgA biotin-labelled goat Fab'2, (0.14 μg/ml final) (Caltag H 14015) and revealed with streptavidine-HRP (1/50,000). A 2F5-IgG monoclonal antibody was used as positive control, followed with a biotinylated anti-human IgG goat Fab'2 (0.1 μg/ml final) (Rockland 609106123) and revealed with streptavidine-HRP (1/50,000). The antibodies were incubated for 1 hour at 37° C. Colorimetric reaction was triggered by addition of the substrate TMB, and stopped by addition of $H_2PO_4$ 1M. The optical density (OD) was read at 450 nm.

Figure 3:
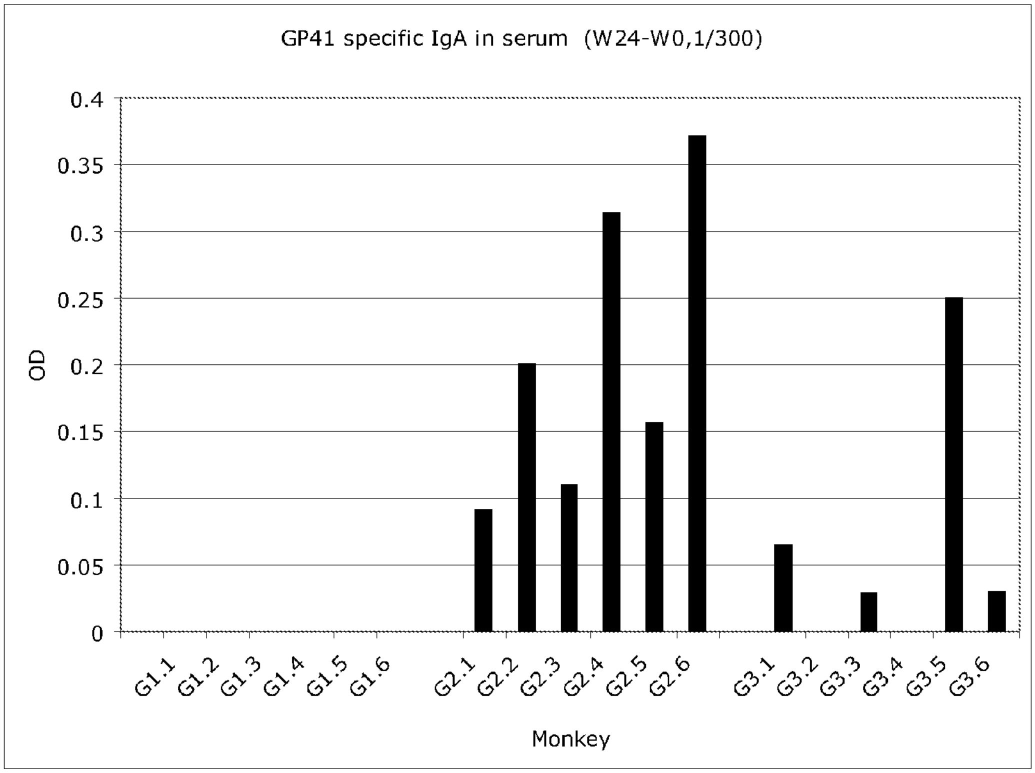
FIG. 3: Shows IgA in serum samples of macaques immunized with rgp41-virosomes and with P1-virosomes by intramuscular injection (monkeys G2.1 through 2.6), compared with serum of macaques immunized with virosomes by combined intramuscular and intranasal injection (G3.1 though 3.6). Group 1 (G1.1-1.6, placebo) is the control group; these animals were immunized intramuscularly with plain influenza virosomes lacking HIV antigens. The data are for serums collected at week 24, and the OD of pre-immune backgrounds (week 0) have been subtracted form the week 24 ODs (w24-w0). Sample dilution 1:300.
Figure 4:
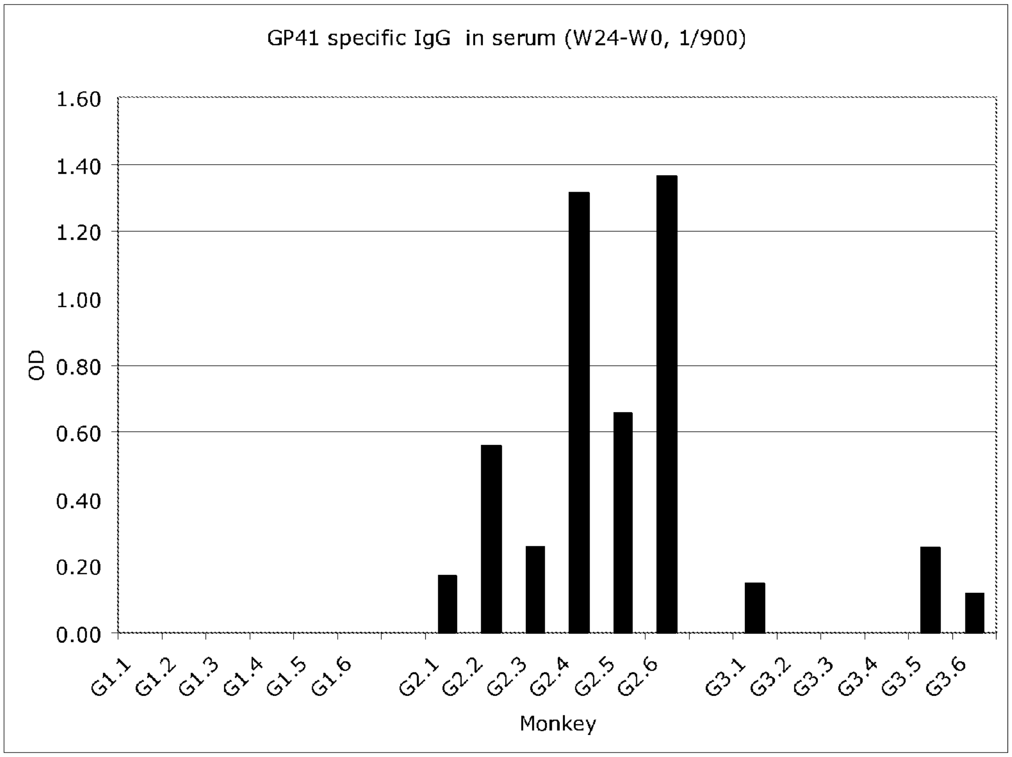
FIG. 4: IgG measured in serum samples from macaques immunized with rgp41-virosomes mixed with P1-virosomes by intramuscular injection (monkeys G2.1 through 2.6), compared with serum of macaques immunized with virosomes by combined intramuscular and intranasal injection (G3.1 though 3.6). Group 1 (monkeys G1.1-1.6) is the control (placebo) group, immunized intramuscularly with influenza virosomes. The data are for serums collected at week 24, and the OD of pre-immune backgrounds (week 0) have been subtracted form the week 24 ODs (w24-w0). Sample dilution 1:900.

The results are illustrated in FIG. 3 (gp41-specific IgA in serum) and FIG. 4 (gp41-specific IgG in serum). Results show that female macaques vaccinated intramuscularly have high levels of specific IgG and IgA anti-gp41 antibodies into their serum. In conclusion, the presence of IgG as well as IgA antibodies was observed in serum from immunized female macaques. The results revealed that an immune response with IgA may be obtained with a vaccine of the invention.

To investigate whether vaccination had induced mucosal immunity, cervico-vaginal samples were obtained from all the vaccinated animals of example 6 at week 24, by introducing 3 ml of PBS containing antibiotics and protease inhibitors. The samples were centrifuged to remove debris, aliquoted, immediately snap-frozen and stored at −80° C. Mucosal P1 antibodies were determined by the ELISA as described above, while clade B anti-gp41 antibodies were determined according to Tudor et al., 2009, Mucosal Immunol. 2, 412-426. The results were expressed as the number of animals having antibody concentrations two times the standard deviation, and compared to the results of serum antibody determinations, expressed in a similar fashion (table I). The serum from monkey 3.2 was excluded from analysis.

TABLE I

| | Anti- | Serum | | | CVS | | |
|---|---|---|---|---|---|---|---|
| Antigen | body | Group 1 | Group 2 | Group 3 | Group 1 | Group 2 | Group 3 |
| P1 | IgA | 0/6 | 2/6 | 0/5 | 0/6 | 3/6 | 4/5 |
| P1 | IgG | 0/6 | 6/6 | 0/5 | | | |
| gp41 | IgA | 0/6 | 6/6 | 4/5 | 0/6 | 2/6 | 2/5 |
| gp41 | IgG | 0/6 | 6/6 | 3/5 | 0/6 | 2/6 | 3/5 |

Additionally, it was observed that the IgA and IgG antibodies were also induced in the genital tract, while IgA was detected in the intestinal compartments, even after vaccination by intramuscular injection in the absence of mucosal adjuvant.

Example 7

Protection Against Heterologous Challenge of the Vaccinated Macaques

Figure 5:
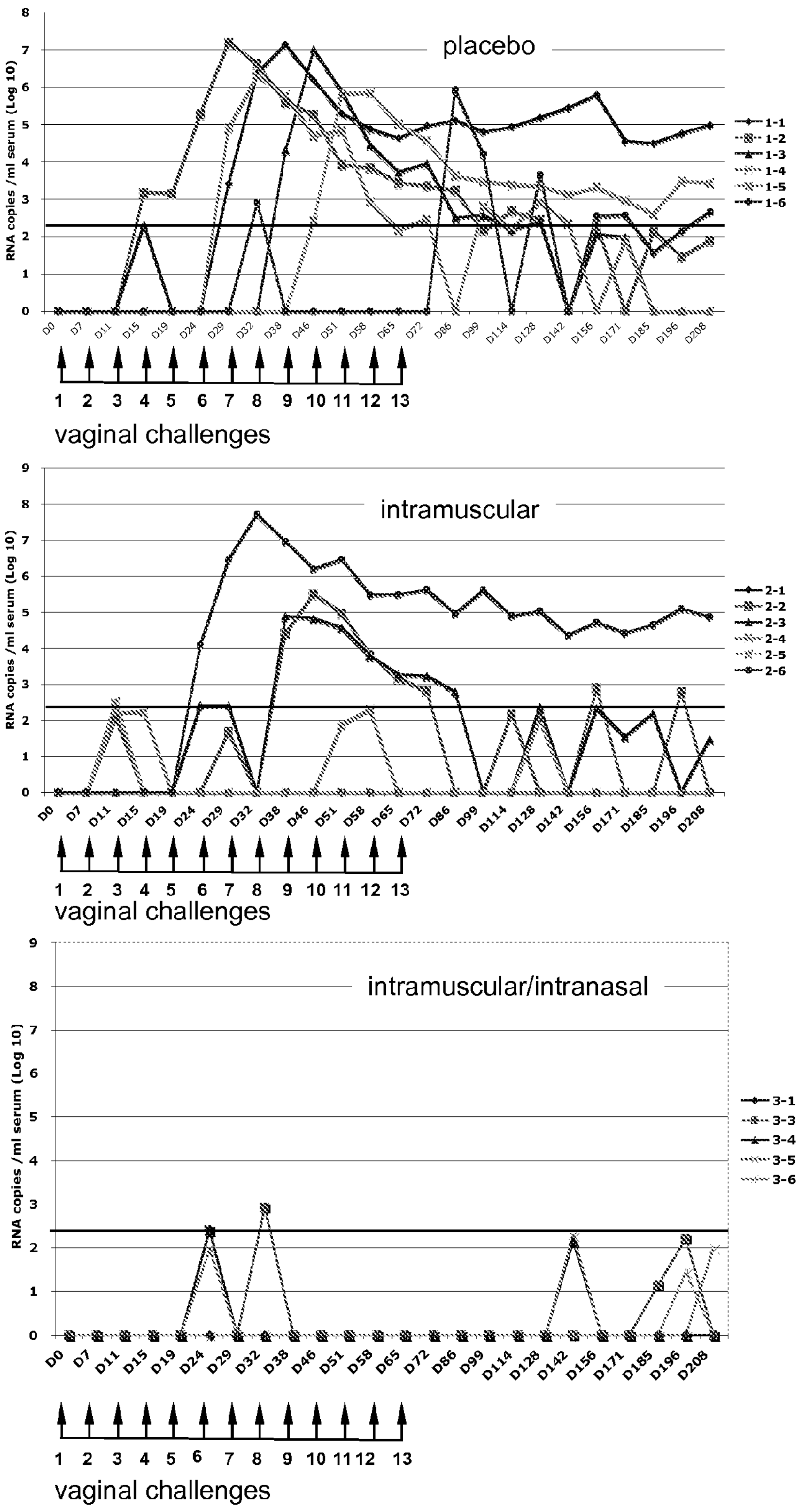
FIG. 5: Viremia during and after intravaginal challenges with SHIVSF162P3 clade B. Arrows indicate the 13 vaginal challenges with 20-30 $TCID_{50}$, starting one month after the last of four vaccinations, the days after initial challenge being denoted by the oblique numbers. The plasma viral load is indicated by the lines for individual animals; the detection limit of $2.5\times10^3$ copies per mL by the straight line. Lines with symbols represent individual animals. groups as in FIGS. 3 and 4.

The monkeys of example 6 were challenged with live virus as follows: Four weeks after the last vaccination, animals were challenged intra-vaginally 13 times, every 4 to 7 days, with low doses (20-30 $TCID_{50}$) of $SHIVSF_{162P3}$, as shown in FIG. 5. This chimeric simian/clade B human immunodeficiency virus has the pathogenic SIVmac239 as a backbone, containing the env (gp120+gp41), tat, rev and vpu genes from HIV-1SF162P3. This virus recognizes the receptor CCR5, in contrast to the X4 tropic HxB2 strain used to derive the gp41-construct of the invention and the peptide P1 of the invention, Therefore, the challenge is with a heterologous virus. The virus was provided by the NIAID (National Institute of Allergy and Infectious diseases), NIH (National Institutes of Health) Bethesda, USA) in 2 mL of PBS.

As shown in FIG. 5, all unvaccinated monkeys (placebo, group 1) were rapidly infected with the virus, with plasma viral loads spiking within two weeks at around $10^6$ to $10^7$ copies per ml, as expected (Hessell, A. J. et al. Nat. Med. 15, 951-959). 50% of the monkeys in group 2 (intramuscular vaccination) were protected. All animals in group 3 (intramuscular/intranasal) were protected; one animal (no. 3.3) had a delayed and low viremia at 800 copies/ml for about one week, and was negative thereafter; to confirm, the assay on the samples was repeated with a lower detection threshold (FIG. 5). One animal in group 3 died for reasons not related to the challenge. These data indicate that vaccination protects animals against heterologous challenge, although group 3 has low levels of systemic neutralizing antibodies.

Example 8

Inhibition of Transcytosis and Cross-Clade Protection

Figure 6:
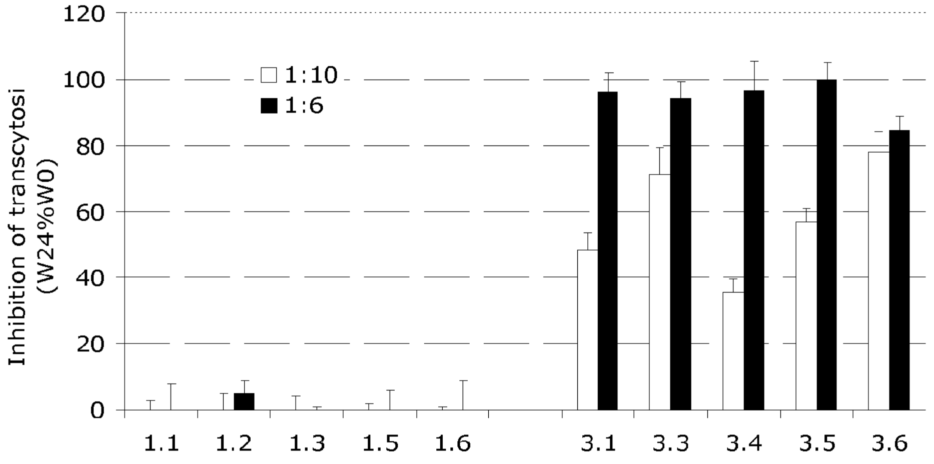
FIG. 6: Inhibition of HIV-1 transcytosis across epithelial cells by cervicovaginal secretions (CVS). Panel A: strain HIV-1 93BR029 (clade B) Panel B: HIV-1 strain 92BR025 (Clade C) Solid bars: CVS used at a 1:6 dilution, open bars 1:10. In the absence of specific IgA antibodies against gp41, transcytosis capability of the HIV-1 is >100% efficient, while in the presence of specific IgA anti-gp41 antibodies, transcytosis can be reduced >40% with CVS diluted 1:6.
Figure 6:
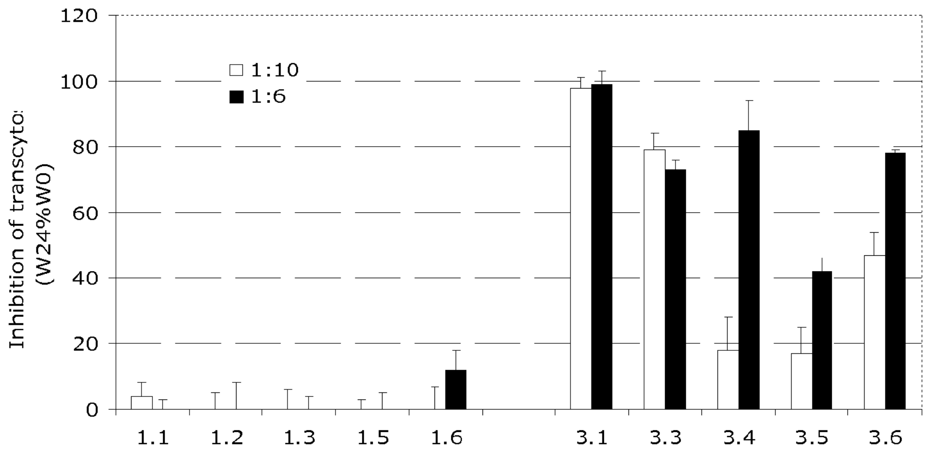

To investigate whether vaccination had induced mucosal immunity, cervico-vaginal samples obtained as described in Example 6, were analyzed by HIV-1 transcytosis inhibition assays, performed as previously described (Bomsel et al., 1997. Nat. Med. 3: 42-47). HIV-I transcytosis across epithelial cells and the neutralization of transcytosis by antibodies were investigated on the intestinal cell line HT 29 grown as a tight, polarized monolayer for 7 days on a permeable filter support (0.45 μm pore size) forming the interface between two independent chambers, the upper one bathing the apical (luminal) surface of the epithelial monolayer and the lower one bathing the basolateral surface. Prior to transcytosis experiments, epithelial cells were washed, and further incubated in RPMI 1640, glutamine, 10% FCS. Cervico-Vaginal Secretion (CVS) samples (1/12 and 1/6 dilution) from Group 1 (placebo) or Group 3 (W24; i.m.+i.n. —see example 7 above) were pre-incubated with HIV-1 infected cells ($1\times10^6$ HIV-1 93BR029 virus (HIV1 clade B) or with 92BR025 virus (HIV1 clade C)+PBMCs (Day 7 post infection of activated PBMCs from healthy individuals with infected with either JRCSF or primary viruses) for 20 min. at RT. Then, HIV-1 infected cells pre-incubated were added to the apical chamber. Contact between HIV-1 infected cells and the epithelial cell monolayer resulted in rapid budding of the HIV-1-virions, followed by HIV particle internalization and transcytosis from the apical to the basolateral side of the epithelial cell monolayer. After 2 h, inhibition of transcytosis by CVS was determined by detection of p24 in the basolateral medium by commercial ELISA (Coulter, Villepinte, France). During the 2 hrs of infected cell contact with epithelial cells, the barrier function of the epithelial monolayer remains intact, precluding penetration of HIV-1 infected cells in the monolayer or translocation of HIV infected cells in the basolateral chamber (1). The HIV-1 transcytosis results are shown in FIG. 6. Clearly, transcytosis of clade B virus was inhibited by the CVS of vaccinated animals. However, surprisingly, vaccination also induced inhibitory activity against clade C virus, as shown by a reduced transcytosis of HIV-1 respective control (cross-clade protection), suggesting the presence of a shared conformational epitope, as the amino acid sequence differs between the used viruses

Example 9

Transcytosis is Inhibited by Secretory IgA in the CVS of Vaccinated Animals

Figure 7:
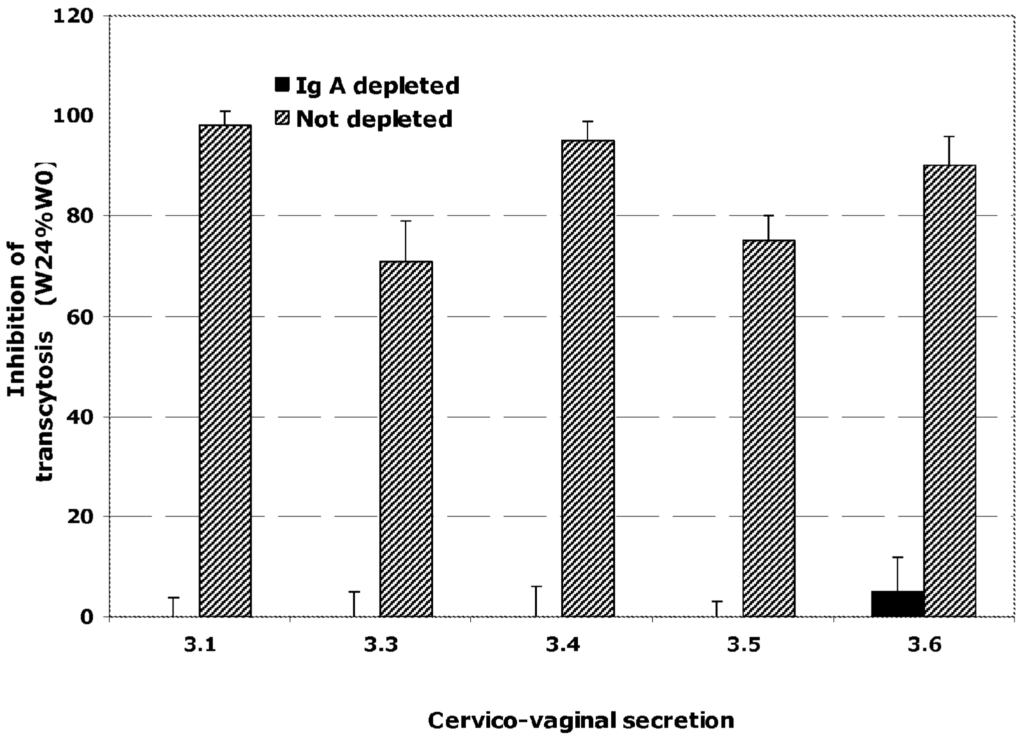
FIG. 7: Inhibition of transcytosis across epithelial cells by CVS secretions, with or without IgA depletion. Solid bars: with depletion, hatched bars without depletion. When CVS contained mucosal IgA antibodies, inhibition of HIV-1 transcytosis could be observed. When IgA was depleted from the CVS, transcytosis inhibition was lost.

Samples of the cervico-vaginal secretions harvested from the animals as described in example 8, were depleted of IgA by incubation with biotinylated-anti macaque IgA antibodies, as follows. Biotinylated anti-human IgA (Caltag, France) was bound to streptavidin-agarose (Pierde, France) in a 1:3 weight ratio, and the coupled beads were washed to remove unbound biotinylated anti-IgA. 30 μl of beads were rotated overnight at 4° C. with CVS (1:6 dilution), and centrifuged for 10 min at 1000 g. The resulting supernatant was collected and assayed followed by an incubation with streptavidin-agarose beads, (Pierde, France) and a centrifugation to remove the beads. These IgA-depleted samples were then tested in a transcytosis assay using clade B 93BR029 virus, as described in example 8, and compared to samples without IgA depletion. As shown in FIG. 7, there was little or no inhibition of HIV-1 transcytosis after depletion of IgA, clearly demonstrating the role of mucosal, rather than serum, IgA in protection against infection.

Example 10

Cross-Clade Protection In Vivo

Figure 8:
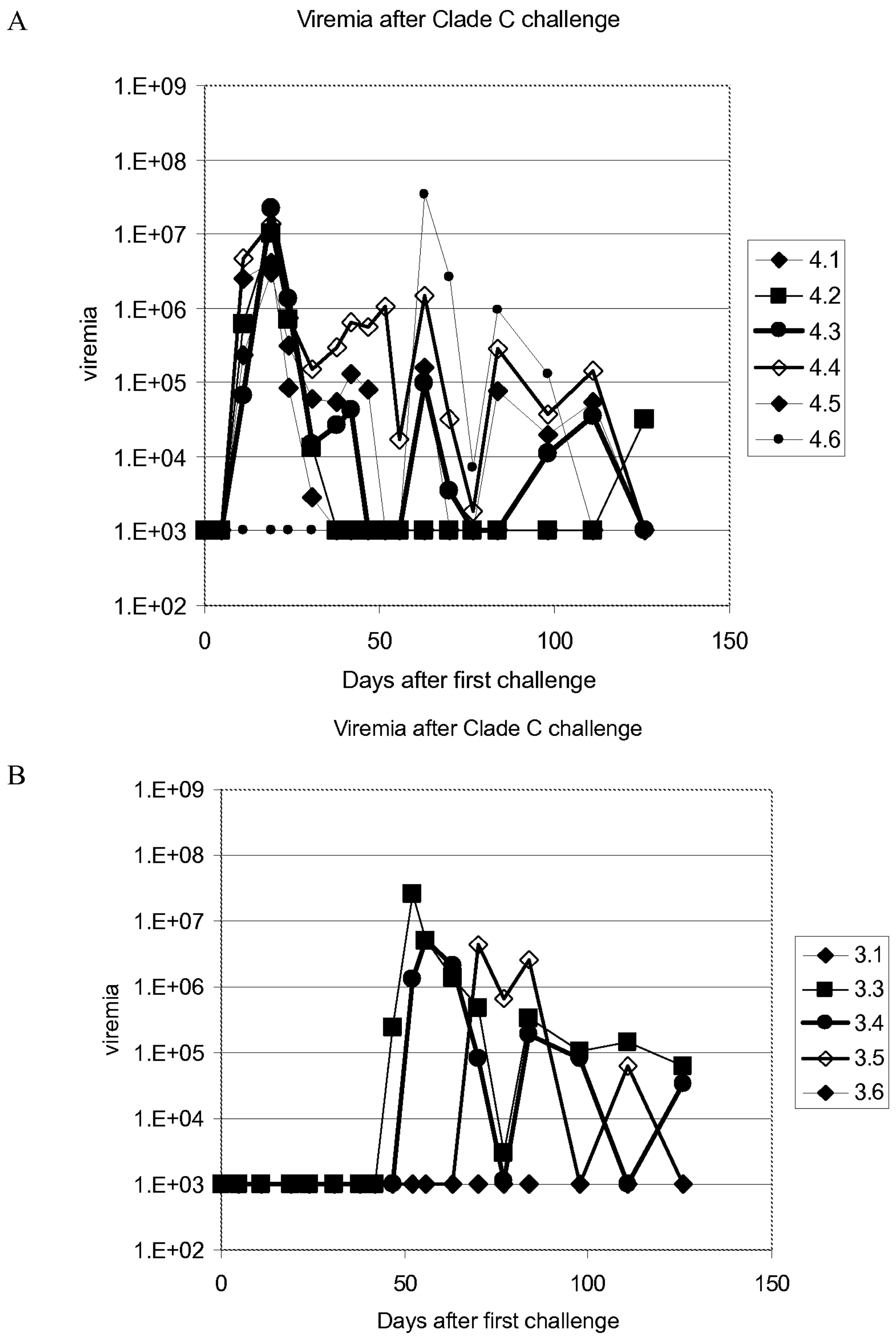
FIG. 8: Panel A: Viremia after Clade C virus challenge, with strain SHIV1157ipd3N4, of unvaccinated monkeys.

Since in vitro cross-clade transcytosis inhibition was observed in assays, as indicated above, it was decided to challenge the monkeys from group 3, example 6 (intranasal and intramuscular vaccination with clade B based virosomes) with a clade C virus. One year after their last vaccination with the virosomes, the monkeys were still seronegative. They were revaccinated once by intramuscular injection as described in Example 6, and five weeks after vaccination they were challenged 10 times, at 4-7 day intervals, with 10-20 $TCID_{50}$ of SHIV1157ipd3N4 (Clade C, tropism R5, kindly provided by Dr. Ruth Ruprecht, Dana Farber Cancer Institute, USA), At each vaccination time point, blood samples were taken to determine viremia. Blood samples were taken every 4-7 days for 60 days thereafter (FIG. 8). As shown in FIG. 8, the first 40 days after infection no vaccinated animals were infected. In a non-vaccinated control group, 5/6 monkeys were infected at day 11 (FIG. 9), and at day 60 all animals were infected. In the vaccinated group, 2/5 monkeys remained uninfected for the 120 days duration of the study, while for those that were infected, it was significantly delayed respective to the control group.

These surprising data provide clear evidence for cross-clade protection in vivo.

The invention claimed is:

1. A method for inducing an immune response in a patient, comprising at least:

a) administering to the patient a first antigen comprising the broadly neutralizing epitopes of the Membrane Proximal External Region (MPER) of gp41, and b) administering to the same patient a second antigen comprising a modified polypeptide comprising three contiguous segments N, L and C represented by the formula N-L-C and comprising:

a N-helix region of gp41 (N), a C-helix region of gp41 (C), and a connecting loop comprising a synthetic linker (L) between the N and C-helices, the linker replacing amino acids 593-617 of gp41 of the prototypic isolate HIV-1 HxB2 Clade B strain, wherein amino acids 522 to 681 of this numbering scheme correspond respectively to amino acids 1 to 142 set forth in SEQ ID NO:1, said polypeptide comprising the calveolin-1 neutralizing and 98.6 D epitopes, but not 2F5 and 4E10 epitopes, not the fusion peptide, the polypeptide having a minimal immunogenic cross-reactivity with human interleukin 2.

2. The method according to claim 1, wherein said first antigen contains the 2F5 and 4E10 epitopes.

3. The method according to claim 2, wherein said first antigen comprises the amino acid segment 649-683 of the gp41 of the prototypic isolate HIV-1 HxB2 Clade B strain.

4. The method according to claim 1, wherein said first antigen comprises a neutralizing IgA epitope.

5. The method according to claim 1, wherein said first antigen comprises the full-length amino acid sequence set forth in one of SEQ ID NOS:2-6.

6. The method according to claim 1, wherein said first antigen is linked to a virosome.

7. The method according to claim 1, wherein said second antigen comprises the full-length amino acid sequence set forth in SEQ ID NO:19 or 20.

8. The method according to claim 1, wherein said second antigen is conjugated with a virosome.

9. The method according to claim 1, wherein the first and second antigens are co-administered to the patient in a same dosage or in respectively different dosages.

10. The method according to claim 1, comprising co-administering said first and second antigens, by at least two different routes of application, at a same time or at respectively different or following times.

11. The method according to claim 9, wherein the first and second antigens are administered by a systemic route and a topical route.

12. The method according to claim 9, wherein the first and second antigens are administered by the same route, at the same time or respectively different or following times.

* * * * *